(12) United States Patent
Bishop et al.

(10) Patent No.: US 8,668,668 B2
(45) Date of Patent: Mar. 11, 2014

(54) EXPANDABLE ILIAC SHEATH AND METHOD OF USE

(75) Inventors: Joseph Bishop, Menifee, CA (US); Jay Lenker, Laguna Beach, CA (US); Edward J. Nance, Corona, CA (US); Huan T. Nguyen, Santa Ana, CA (US); Mark T. Jones, Garden Grove, CA (US)

(73) Assignee: Onset Medical Corporation, Irvine, CA (US)

( * ) Notice: Subject to any disclaimer, the term of this patent is extended or adjusted under 35 U.S.C. 154(b) by 557 days.

(21) Appl. No.: 12/258,233

(22) Filed: Oct. 24, 2008

(65) Prior Publication Data

US 2009/0287182 A1 Nov. 19, 2009

Related U.S. Application Data

(60) Provisional application No. 61/127,619, filed on May 14, 2008.

(51) Int. Cl.
*A61M 31/00* (2006.01)
*A61M 37/00* (2006.01)
*A61M 5/178* (2006.01)

(52) U.S. Cl.
USPC .................... 604/103.06; 604/164.1; 604/509

(58) Field of Classification Search
USPC .............................. 604/509, 103.03, 101.01, 604/103.05–103.06, 99.4
See application file for complete search history.

(56) References Cited

U.S. PATENT DOCUMENTS

| 4,338,942 A | 7/1982 | Fogarty |
| 4,401,433 A | 8/1983 | Luther |

(Continued)

FOREIGN PATENT DOCUMENTS

| EP | 0206553 | 1/1991 |
| JP | 2008-512212 | 4/2008 |

(Continued)

OTHER PUBLICATIONS

International Search Report for Application No. PCT/US2009/044031, the PCT counterpart of the present application, mailed Dec. 22, 2009.

(Continued)

*Primary Examiner* — Nicholas Lucchesi
*Assistant Examiner* — Rebecca E Eisenberg
(74) *Attorney, Agent, or Firm* — Knobbe, Martens, Olson & Bear LLP

(57) ABSTRACT

Disclosed is an expandable transluminal sheath, for introduction into the body while in a first, small cross-sectional area configuration, and subsequent expansion of at least a part of the distal end of the sheath to a second, enlarged cross-sectional configuration. The sheath is configured for use in the vascular system and has utility in the introduction and removal of implant delivery catheters. The access route is through the femoral arteries and the iliac arteries into the aorta. The distal end of the sheath is maintained in the first, low cross-sectional configuration during advancement to the arteries into the aorta. The distal end of the sheath is subsequently expanded using a radial dilatation device, which is removed prior to the introduction of implant delivery catheters. In an exemplary application, the sheath includes a supported proximal end, a supported distal end, and a collapsible center section. Certain configurations of the sheath are capable of being inserted in a first, small cross-sectional configuration, being expanded diametrically to a second, larger cross-sectional configuration, and then being reduced to a diametrically small size for removal.

27 Claims, 14 Drawing Sheets

(56) References Cited

U.S. PATENT DOCUMENTS

| | | |
|---|---|---|
| 4,738,666 A | 4/1988 | Fuqua |
| 4,753,221 A | 6/1988 | Kensey et al. |
| 4,919,647 A | 4/1990 | Nash |
| 5,053,007 A | 10/1991 | Euteneuer |
| 5,059,183 A | 10/1991 | Semrad |
| 5,092,839 A | 3/1992 | Kipperman |
| 5,201,901 A | 4/1993 | Harada et al. |
| 5,250,025 A | 10/1993 | Soanowski et al. |
| 5,263,964 A | 11/1993 | Purdy |
| 5,295,994 A | 3/1994 | Bonutti |
| 5,320,611 A | 6/1994 | Bonutti |
| 5,358,495 A | 10/1994 | Lynn |
| 5,395,349 A | 3/1995 | Quiachon et al. |
| 5,458,574 A | 10/1995 | Machold et al. |
| 5,514,091 A | 5/1996 | Yoon |
| 5,527,336 A | 6/1996 | Rosenbluth |
| 5,662,614 A | 9/1997 | Edoga |
| 5,669,936 A | 9/1997 | Lazarus |
| 5,766,151 A | 6/1998 | Valley et al. |
| 5,766,203 A | 6/1998 | Imran et al. |
| 5,772,631 A | 6/1998 | Lepor |
| 5,776,141 A | 7/1998 | Klein et al. |
| 5,807,311 A | 9/1998 | Palestrant |
| 5,814,016 A | 9/1998 | Valley et al. |
| 5,824,002 A | 10/1998 | Gentelia et al. |
| 5,868,702 A | 2/1999 | Stevens et al. |
| 5,885,238 A | 3/1999 | Stevens et al. |
| 5,908,448 A | 6/1999 | Roberts et al. |
| 5,911,702 A | 6/1999 | Romley et al. |
| 5,928,181 A | 7/1999 | Coleman et al. |
| 6,090,096 A | 7/2000 | St Goar et al. |
| 6,129,707 A | 10/2000 | Cryer |
| 6,139,517 A | 10/2000 | Macoviak et al. |
| 6,149,578 A | 11/2000 | Downey et al. |
| 6,152,141 A | 11/2000 | Stevens et al. |
| 6,156,053 A | 12/2000 | Gandhi et al. |
| 6,168,579 B1 | 1/2001 | Tsugita |
| 6,183,443 B1 | 2/2001 | Kratoska et al. |
| 6,197,016 B1 | 3/2001 | Fourkas et al. |
| 6,231,498 B1 | 5/2001 | Pfeiffer et al. |
| 6,231,551 B1 | 5/2001 | Barbut et al. |
| 6,234,995 B1 | 5/2001 | Peacock, III |
| 6,254,563 B1 | 7/2001 | Macoviak et al. |
| 6,264,633 B1 | 7/2001 | Knorig |
| 6,299,628 B1 | 10/2001 | Harrison et al. |
| 6,312,443 B1 | 11/2001 | Stone |
| 6,338,725 B1 | 1/2002 | Hermann et al. |
| 6,346,092 B1 | 2/2002 | Leschinsky |
| 6,358,238 B1 | 3/2002 | Sherry |
| 6,368,345 B1 | 4/2002 | Dehdashtian et al. |
| 6,375,675 B2 | 4/2002 | Dehdashtian et al. |
| 6,451,053 B1 | 9/2002 | Dehdashtian et al. |
| 6,530,894 B1 | 3/2003 | Barbut |
| 6,537,247 B2 | 3/2003 | Shannon |
| 6,547,760 B1 | 4/2003 | Samson et al. |
| 6,565,552 B1 | 5/2003 | Barbut |
| 6,576,007 B2 | 6/2003 | Dehdashtian et al. |
| 6,579,259 B2 | 6/2003 | Stevens et al. |
| 6,582,388 B1 | 6/2003 | Coleman et al. |
| 6,592,557 B2 | 7/2003 | Barbut |
| 6,616,678 B2 | 9/2003 | Nishtala et al. |
| 6,626,899 B2 | 9/2003 | Houser et al. |
| 6,635,046 B1 | 10/2003 | Barbut |
| 6,638,268 B2 | 10/2003 | Niazi |
| 6,669,687 B1 | 12/2003 | Saadat |
| 6,679,871 B2 | 1/2004 | Hahnen |
| 6,692,512 B2 | 2/2004 | Jang |
| 6,695,810 B2 | 2/2004 | Peacock, III et al. |
| 6,695,811 B2 | 2/2004 | Samson et al. |
| 6,695,864 B2 | 2/2004 | Macoviak et al. |
| 6,706,013 B1 | 3/2004 | Bhat et al. |
| 6,706,017 B1 | 3/2004 | Dulguerov |
| 6,712,806 B2 | 3/2004 | St. Germain et al. |
| 6,726,651 B1 | 4/2004 | Robinson et al. |
| 6,743,196 B2 | 6/2004 | Barbut et al. |
| 6,746,431 B2 | 6/2004 | Pfeiffer et al. |
| 6,767,345 B2 | 7/2004 | St. Germain et al. |
| 6,793,647 B1 | 9/2004 | Cryer |
| 6,796,992 B2 | 9/2004 | Barbut |
| 6,848,448 B1 | 2/2005 | St. Germain et al. |
| 6,866,647 B2 | 3/2005 | Barbut |
| 6,866,650 B2 | 3/2005 | Stevens et al. |
| 6,872,223 B2 | 3/2005 | Roberts et al. |
| 6,913,600 B2 | 7/2005 | Valley et al. |
| 6,932,792 B1 | 8/2005 | St. Goar et al. |
| 7,150,736 B2 | 12/2006 | Barbut et al. |
| 7,229,403 B2 | 6/2007 | Schock et al. |
| 7,309,334 B2 | 12/2007 | Von Hoffmann |
| 7,329,268 B2 | 2/2008 | Van Nguyen et al. |
| 7,635,386 B1 | 12/2009 | Gammie |
| 7,699,864 B2 | 4/2010 | Kick et al. |
| 7,713,193 B2 | 5/2010 | Nance et al. |
| 7,722,568 B2 | 5/2010 | Lenker et al. |
| 7,780,692 B2 | 8/2010 | Nance et al. |
| 7,892,203 B2 | 2/2011 | Lenker et al. |
| 7,914,555 B2 | 3/2011 | Nguyen et al. |
| 8,034,072 B2 | 10/2011 | Nguyen et al. |
| 2001/0012950 A1 | 8/2001 | Nishtala et al. |
| 2002/0009535 A1 | 1/2002 | Michal et al. |
| 2002/0077653 A1 | 6/2002 | Hudson et al. |
| 2002/0099431 A1 | 7/2002 | Armstrong et al. |
| 2003/0114913 A1 | 6/2003 | Spenser et al. |
| 2004/0006344 A1 | 1/2004 | Nguyen et al. |
| 2005/0049667 A1 | 3/2005 | Arbefeuille et al. |
| 2005/0085842 A1 | 4/2005 | Eversull et al. |
| 2005/0124937 A1 | 6/2005 | Kick et al. |
| 2005/0149105 A1 | 7/2005 | Leeflang et al. |
| 2005/0154442 A1 | 7/2005 | Eidenschink et al. |
| 2005/0222576 A1 | 10/2005 | Kick et al. |
| 2005/0251094 A1* | 11/2005 | Peterson .................. 604/164.03 |
| 2006/0074476 A1 | 4/2006 | Holman et al. |
| 2006/0074484 A1 | 4/2006 | Huber |
| 2006/0135962 A1 | 6/2006 | Kick et al. |
| 2006/0135981 A1 | 6/2006 | Lenker et al. |
| 2007/0060880 A1 | 3/2007 | Gregorich et al. |
| 2007/0135793 A1 | 6/2007 | Barbut et al. |
| 2008/0082079 A1 | 4/2008 | Braga et al. |
| 2008/0109065 A1 | 5/2008 | Bowe |
| 2008/0177142 A1 | 7/2008 | Roskopf |
| 2008/0183136 A1* | 7/2008 | Lenker et al. ............ 604/164.03 |
| 2009/0287182 A1 | 11/2009 | Bishop et al. |
| 2009/0287183 A1 | 11/2009 | Bishop et al. |
| 2010/0228077 A1 | 9/2010 | Lenker et al. |
| 2011/0144690 A1 | 6/2011 | Bishop et al. |
| 2011/0152763 A1 | 6/2011 | Bishop et al. |

FOREIGN PATENT DOCUMENTS

| | | |
|---|---|---|
| WO | WO/99/17665 | 4/1999 |
| WO | WO/03/090834 | 11/2003 |
| WO | WO 2006/029370 | 3/2006 |

OTHER PUBLICATIONS

Office Action for JP Application No. 2011-509718 mailed Aug. 6, 2013 (Japanese Counterpart of the present application).

Sep. 15, 2011 Extended Search Report for Application No. 09747627.9 filed on May 14, 2009 (European Counterpart of the present application).

Dec. 28, 2011 International Search Report and Written Opinion of PCT Application No. PCT/US2011/032995 filed on Apr. 19, 2011.

* cited by examiner

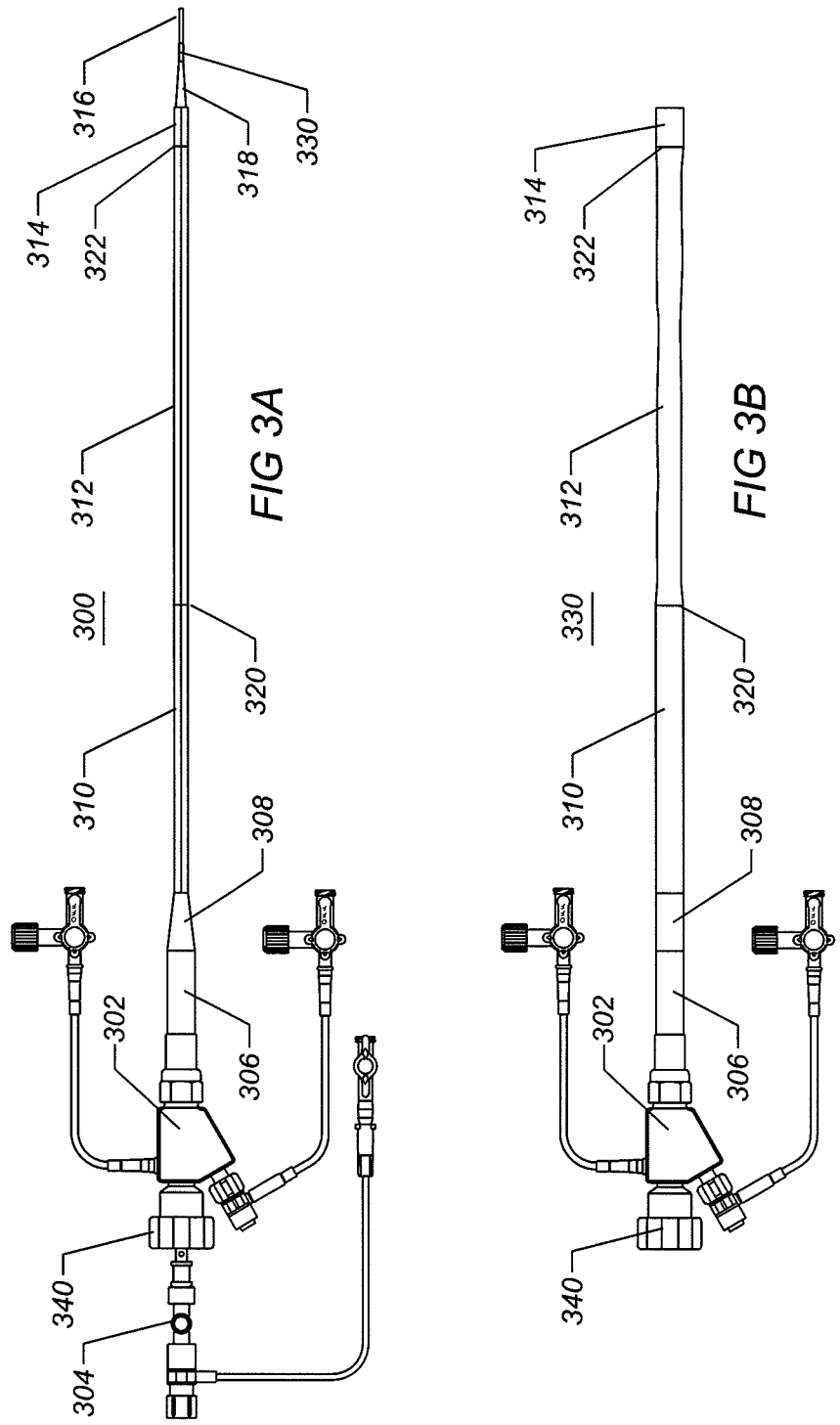

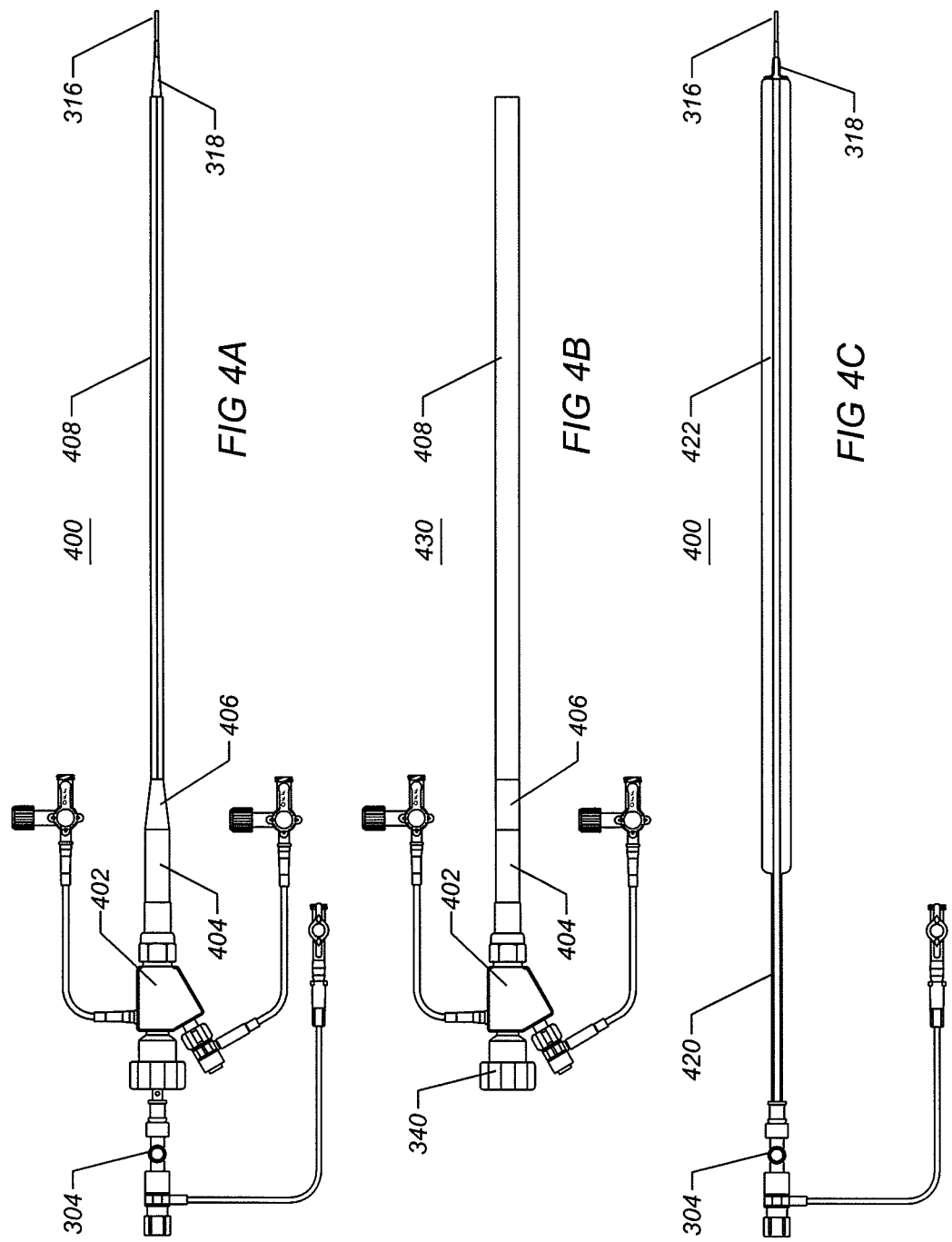

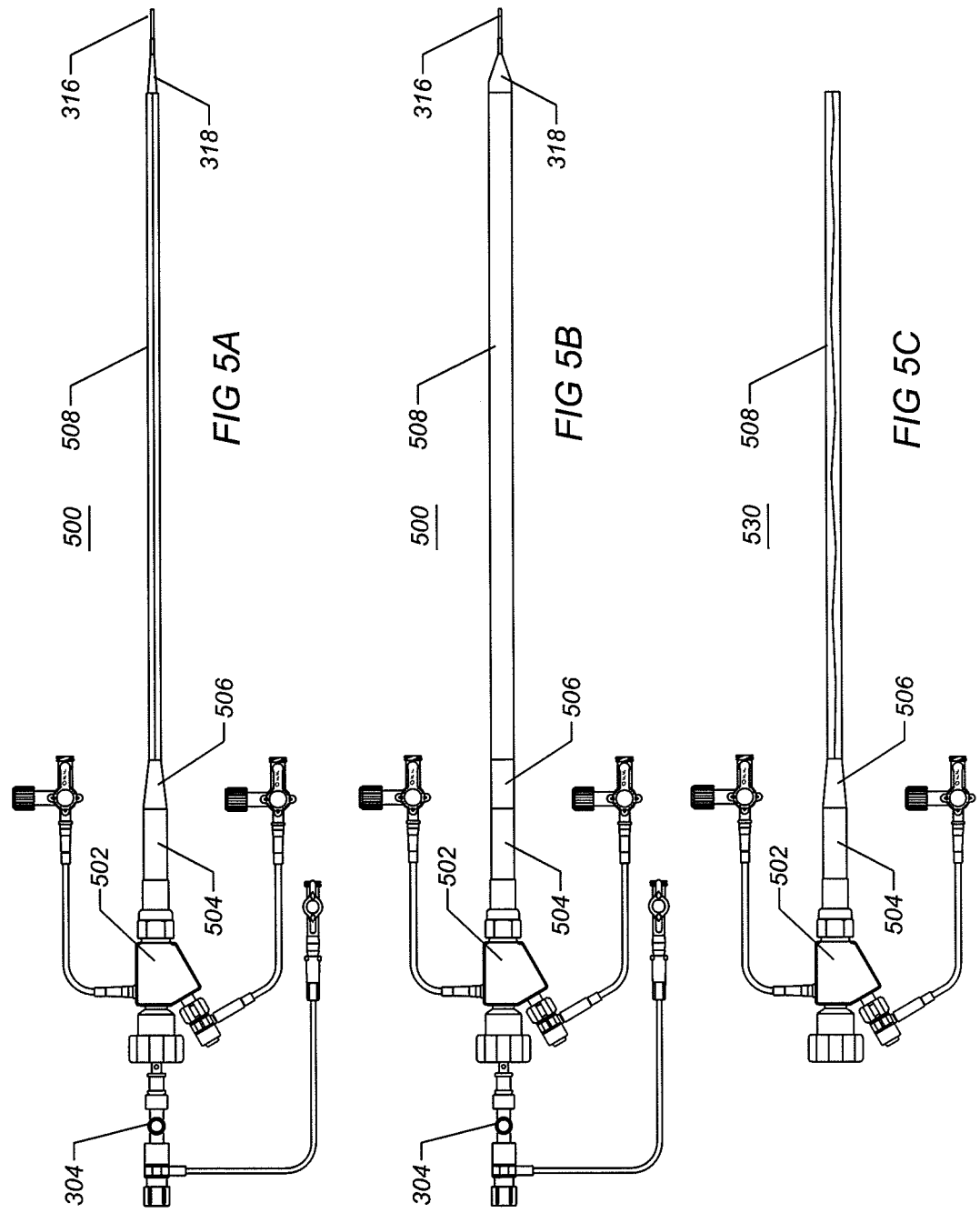

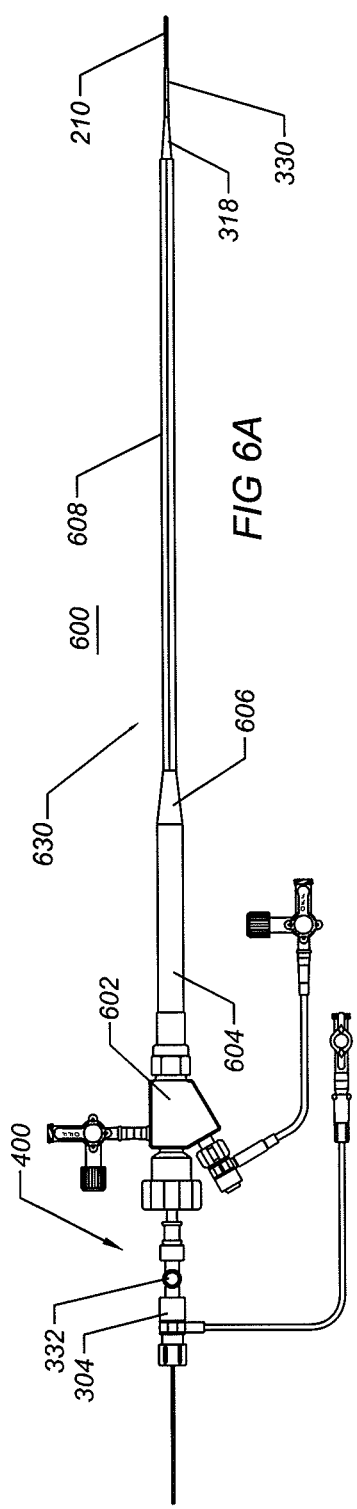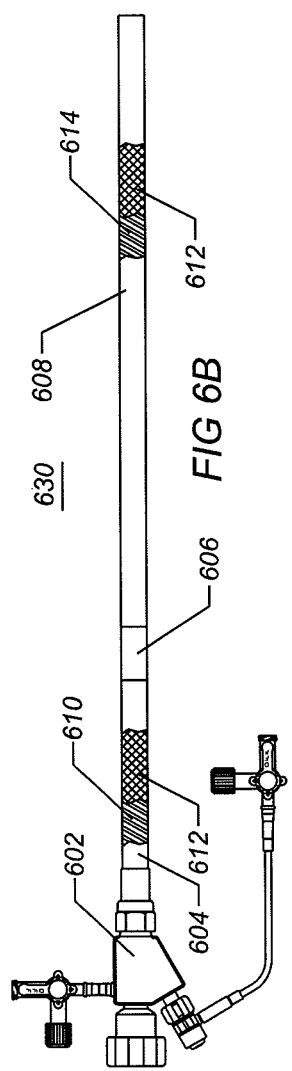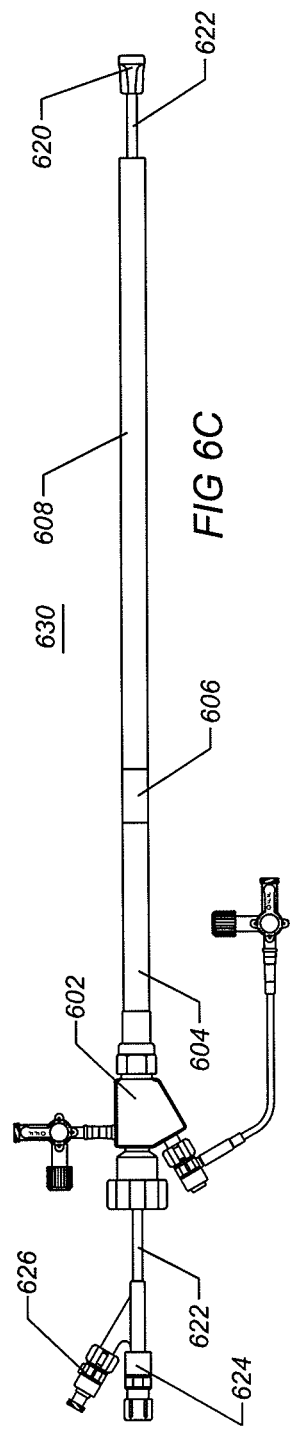

EXPANDABLE ILIAC SHEATH AND METHOD OF USE

PRIORITY CLAIM

This application claims priority to U.S. Provisional Patent Application Ser. No. 61/127,619, filed May 14, 2008, titled Expandable Iliac Sheath and Method of Use and U.S. patent application Ser. No. 12/021,097, filed Jan. 28, 2008, titled Expandable Intra Aortic Balloon Pump Sheath, the entirety of which are hereby incorporated herein by reference.

BACKGROUND OF THE INVENTION

1. Field of the Invention

The present invention relates to medical devices for percutaneously accessing body lumens and, more particularly, to methods and devices for accessing the cardiovascular system.

2. Description of the Related Art

A wide variety of diagnostic or therapeutic procedures involve the introduction of a device into the vasculature through a percutaneous or open surgical incision at an access site. Such regions of the vasculature, preferred for access, include both the iliac, subclavian, and femoral arteries. A percutaneous technique commonly known for such vascular access is the Seldinger technique. The Seldinger technique involves using a hollow needle to puncture the skin and gain access to the selected artery or vein. A guidewire is next placed through the hollow needle into the selected region of vasculature. The guidewire may be advanced to a target location in the vasculature, which can be more than 100 cm away from the access site. The needle is removed and a tapered dilator with a sheath and a central lumen in the dilator is advanced over the guidewire into the vasculature. The dilator is next removed and a guide catheter is advanced through the sheath over the guidewire. The guide catheter can be advanced all the way, or part way, to the target site. The guide catheter, following, or without, removal of the guidewire can be used for directing therapeutic or diagnostic catheters to regions of the vasculature and central circulation, including external and internal structures of the heart. A general objective of access systems, which have been developed for this purpose, is to minimize the cross-sectional area of the access lumen, while maximizing the available space for the diagnostic or therapeutic catheter placement therethrough. These procedures are especially suited for coronary angioplasty, stent placement, cardiac valve replacement, stent-graft placement, cerebrovascular embolic coil placement, diagnostic cardiac catheterization, cardiac assist, and the like.

One type of cardiac procedure involves placement of a collapsible cardiac valve in either the aortic, tricuspid, or mitral position. Today, an aortic valve replacement procedure involves the steps of inserting a hollow needle, with a hemostasis valve affixed to its proximal end, into the femoral or iliac artery of a patient via a percutaneous puncture. A guidewire is next inserted through the hemostasis valve and the central lumen of the needle into the femoral or iliac artery. The guidewire is routed, under fluoroscopic control, cranially toward the heart, through the aortic arch, through the aortic valve and into the left ventricle. The hollow needle is removed from the patient leaving the guidewire in place. An introduction sheath, including a tapered tip central obturator or dilator having a hemostasis valve at its proximal end and further including a central guidewire lumen is routed over the guidewire, through the skin puncture, through the wall of the artery, and into the central lumen of the iliac artery or aorta. The central obturator or dilator is removed. A valve delivery catheter is next advanced over the guidewire and through the introduction sheath to the region of the aortic root. The aortic valve is deployed in the region of the aortic root such that the remnants of the original valve are outwardly dilated by the implant, which comprises a valve and expandable support stent. The valve is seated firmly so as to become secured to the aortic valve remnant. The delivery catheter is next removed from the patient leaving the new valve in place. The sheath is next removed and hemostasis is established using standard techniques for a vessel puncture wound. Indications for percutaneous valve replacement include a stenotic or incompetent aortic valve and a contraindication to open surgical valve replacement.

Issues can arise, however, when the delivery catheter or sheath are removed from the patient. Withdrawal of large catheters and sheaths has been reported to cause disruption of vessel plaque during removal or pullback through the aorta, iliac and femoral arteries. This is especially problematic in very sick patients with significant vascular disease that involves plaque, mural thrombus, aneurysms, and other pathologies. The disruption of a region of plaque or thrombus can cause emboli to break free from the vessel wall, float downstream, and lodge within the lumen of smaller distal vessels, blocking blood flow, and resulting in ischemia and possibly tissue necrosis. Not only during withdrawal, but also during insertion, do issues arise with insertion of sheaths and catheters. In patients suffering form substantial cardiovascular disease, atheroma, thrombus, and other plaque can build up on the interior of the abdominal aorta, iliac arteries, and femoral arteries. These vessels can have their lumen diameters substantially reduced by these buildups and furthermore, the vessels can become highly tortuous. Thus, insertion of catheters, especially large diameter catheters and introducer sheaths can be difficult or impossible because of vessel stenosis or wall interference.

Suggested further reading related to the use of iliac or femoral introducers for large catheters includes Gawenda M, and Brunkwall J, Device-Related Problems of Thoracic Stent-Grafts, 1: *Zentralbl Chir.* June 2007; 132(3):205-10, the entirety of which is hereby incorporated by reference herein.

It is desirable to protect the arteries, including the femoral and iliac arteries, from a delivery catheter and sheath during removal. A need remains, therefore, for improved access technology, which allows a large diameter catheter or sheath to be percutaneously or surgically introduced through the iliac, femoral, or subclavian arteries, and then be removed without causing further injury or complications to the patient.

SUMMARY OF THE INVENTION

One arrangement comprises an introducer sheath having a first, smaller cross-sectional area and a second, larger cross-sectional area. The introducer sheath can comprise a hub and a length of sheath tubing. The sheath tubing and the hub form an axially elongate structure having a proximal end, a distal end, a wall, and a lumen extending from approximately the proximal end to the distal end. In certain embodiments, the sheath tubing has a proximal section, a central section, and a distal section. The proximal section can be partially expandable, fully expandable, or completely non-expandable, diametrically. In an embodiment, the distal section can be expandable. The introducer sheath is suitable for iliac access, femoral access, trans-femoral access, subclavian artery access, or aortic access.

The sheath can be used as an introducer for long guiding sheaths, other expandable sheaths, or catheter systems. The expandable sheath has the clinical benefit of being able to radially dilate tissue, thus causing minimal tearing and tissue trauma. The expandable sheath can be used to assist with percutaneous vascular access procedures in that it allows for a small diameter access to the femoral, iliac, or subclavian arteries that can then be expanded into a size large enough for introduction of large interventional, therapeutic, or diagnostic devices therethrough. Interventional cardiologists generally prefer to perform interventional procedures where the access is percutaneous and does not require a surgical cutdown. Should a surgical cutdown be required for access, a surgeon is generally brought in to perform the access. The expandable arterial access sheath can eliminate the need for a cutdown and the surgical support, reducing time, procedure cost, trauma to the patient, and improving patient outcomes.

In certain arrangements, the central section can be expandable. In some arrangement, the central section can comprise a polymeric wall with reinforcing elements that maintain the cross-sectional shape of the central section prior to expansion, and after expansion. In other arrangement, the central section can comprise a polymeric wall that is non-distensible but otherwise foldable and free from any reinforcing elements. In these non-reinforced embodiments, the central section can possess the properties of flexibility but have minimal structure and thus, cannot maintain a cross-sectional shape. In some arrangements, the central section can comprise longitudinally disposed reinforcing elements that provide column strength and tensile strength but offer little or no cross-sectional shape retention.

In some arrangements, the distal section can comprise a polymeric wall with reinforcing elements that provide a degree of retention of cross-sectional shape. The distal section can comprise weak reinforcing elements that provide some control over the shape of the polymeric wall but are easily deformed into a collapsed configuration upon exposure to external forces such as those imposed by a blood vessel wall. The distal section can comprise polymeric materials that can be plastically deformed and do not substantially spring back following dilation. In these embodiments, the distal end is subject to remodeling by inflation of the expansion balloon under pressures ranging between 10 and 40 atmospheres.

In other arrangements, the distal end of the sheath can comprise a flared component that becomes larger in diameter moving distally. The flared component can comprise a taper, or it can comprise a taper and a region of relatively constant diameter affixed or integral to the tapered region at its most distal end. The flared component can be integral to the distal end of the expandable portion of the sheath, or it can be affixed thereto. The flared component can be expanded using a balloon dilator, it can be expanded using self-expansion modalities, or it can comprise self-expansion with balloon dilator assist. The self-expansion can be due to resilient spring forces, or due to shape memory forces generated by sheath reinforcement components fabricated from nitinol, or other shape memory materials. The flared configuration can facilitate re-capture or removal of instruments or implantable devices such as percutaneously delivered aortic heart valves. In an exemplary embodiment, the flared configuration can also facilitate removal of the natural aortic valve root, should excision of the aortic valve root be required. The expandable, flared region of the sheath can range in length between 1-cm and 10-cm, with a preferred range of 2-cm to 5-cm. In an embodiment, the flared region can use the same balloon as the rest of the distal expandable region for expansion, or it can be expanded by a separate balloon.

In some arrangements, the proximal end of the sheath can comprise a hub incorporating one or more hemostasis-type valves. The hub can comprise a single catheter insertion port or it can comprise a plurality of catheter insertion ports. Each catheter insertion port preferably comprises hemostasis valves, stopcocks, or the like to prevent blood leakage from the catheter. The hub can further comprise one or more purge ports, which operably connect to the internal lumen of the hub and are terminated by stopcocks or other valve.

In some arrangements, the diametrically or radially expandable elements of the catheter can be configured as a tube having a plurality of longitudinal folds. The expandable regions or elements, located in the proximal section, distal section, or the center section of the sheath or catheter, can be creased into these folds and bent to form a first, smaller, folded cross sectional area. The expandable regions or elements can be folded over a central dilator catheter comprising, for example, an angioplasty-type balloon, a catheter shaft, a balloon inflation port at the proximal end, a guidewire lumen, and the like. Upon selective inflation of the angioplasty-type, non-elastomeric, non-distensible, balloon by application of fluid pressure into an appropriate port on the proximal end of the dilator catheter, the expandable regions can unfold into a second, larger, cross-sectional shape. The central dilator catheter can be deflated and removed from the sheath to create a large cross-section center lumen suitable for the introduction of catheters, delivery catheters, implantable devices, and the like.

In an exemplary embodiment, the expandable introducer sheath comprises a proximal, expandable section. The proximal expandable section comprises a composite tubular structure fabricated from an inner polymeric layer of polyethylene, an outer polymeric layer of polyethylene, and a reinforcement layer sandwiched between the two polymer layers. The reinforcement layer can comprise a coil of flat, fully annealed, stainless steel wire with a width of about 0.010 inches, with a range of 0.005 to 0.025 inches, and a thickness of about 0.003 inches, with a range of 0.002 to 0.004 inches. The proximal, expandable region is affixed at its proximal end to a non-expandable length of sheath tubing of the same or similar inside diameter, or it is affixed directly to the sheath hub. The distal end of the proximal expandable region is affixed to a central expandable region that comprises inelastic polymeric materials. The central expandable region can comprise a membrane of polymers bonded, welded, or surrounding a braid, or other fabric reinforcing structure that provides a level of column strength and a level of tensile strength for the central expandable region. The distal end of the central expandable region is affixed to a distal expandable region configured similarly to the proximal expandable region except that the distal expandable region is somewhat weaker so that it is easily collapsed, following expansion.

In another embodiment, the sheath tubing can comprise a proximal region wherein a reinforcing layer of spring stainless steel ribbon is wound into a coil with a width of about 0.005 to 0.025 inches and a thickness of about 0.002 to 0.004 inches. The coil spacing can range between 0.001 inches and 0.050 inches.

In another embodiment, the sheath can comprise a proximal non-expandable region and a distal expandable region. The distal expandable region can comprise between 10% and 95% of the catheter shaft length.

The distal, expandable region can comprise a reinforcing layer of malleable stainless steel ribbon or flat wire wound into a coil with similar dimensions as in the proximal region. The entire length, or a substantial portion thereof, can comprise an additional reinforcing layer, or layers, of braided material fabricated from materials such as, but not limited to, PEN, polyester, stainless steel, titanium, nitinol, cobalt nickel alloy, polyamide, polyimide, or the like. In one arrangement, the reinforcing structure, generally sandwiched between an outer and an inner layer of polymeric wall, can comprise an inner layer of polymer overlaid by a first reinforcing braid layer, overlaid by a coil reinforcement, finally overlaid with an outside layer of polymeric material. In another embodiment, the inner layer of polymeric material is overlaid by the coil reinforcement, which is overlaid by the braided reinforcement, which is finally overlaid with the outside layer of polymeric material. In yet another embodiment, the inner layer of polymeric material is overlaid by the braided layer, which is overlaid by the coil winding, which is overlaid by another layer of braid, which is finally overlaid by the outer polymeric layer.

In one embodiment, the sheath dilator is configured with a PET balloon affixed to a Hytrel shaft. The Hytrel shaft can comprise an inner and an outer tube concentrically disposed with an annulus between the two tubes. The distal end of the dilator balloon can be affixed to the inner Hytrel tubing. The proximal end of the dilator balloon is larger in diameter and is affixed to the outer Hytrel tubing in this embodiment. The outer Hytrel tubing extends just inside the center volume of the dilator balloon and the annulus between the outer tube and the inner tube is in fluid communication, operably connected to, the center volume of the dilator balloon. The annulus is operably in fluid communication with an inflation port integral to, or affixed to, the dilator hub. In another embodiment, an outer polymer tube, such as the outer Hytrel tube of the preceding embodiment, can be omitted and the dilator balloon can comprise a proximal tail that extends proximally to bond and seal within the dilator hub or sidearm. In this embodiment, the pressurization annulus for the balloon resides between the dilator balloon and the inner polymer tube, the pressurization annulus being operably connected to an inflation port on the dilator hub. The interior of the inner dilator tube comprises a guidewire lumen suitable for advancing the entire system over a guidewire suitable for aortic access. Such aortic access guidewires typically are 0.035 or 0.038 inches in diameter and are relatively stiff.

The sheath can be folded into one or more longitudinally oriented folds and wrapped around the dilator, with collapsed dilator balloon. The malleable elements in the proximal and distal expandable regions maintain the configuration of the system in its collapsed state. An optional outer jacket, which can have attached, peel-away, tear-away, or removable before use configurations, can be used to encase part or all of the diametrically collapsed sheath tubing. In other embodiments, the sheath can further comprise a thin FEP, PFA, or PTFE tube over the outside of the sheath. This fluoropolymer outer covering need not be removed, its function being to protect a soft polyethylene sheath material from hard vascular deposits such as atheroma.

In yet another embodiment, the central region can comprise elastomeric polymer structure with an optional braid reinforcement that permits the central region to simply expand diametrically from a first smaller diameter to a second larger diameter without the use of folds. An internal slip layer of PTFE, FEP, PFA, or other highly lubricious material can be used to facilitate passage of a catheter through the central region to prevent clinging. The internal slip layer can be the inner layer of the polymer sandwich within which the reinforcing coils or braids are embedded.

Once the expandable introducer sheath has been advanced so that its distal end reaches just above the aortic bifurcation, the dilator is expanded at pressures of between 10 and 40 atmospheres, and preferably between 15 and 30 atmospheres. The dilator is next deflated and removed from the central lumen of the sheath.

In other embodiments, the sheath can comprise a flexible shaft configured with an elastomeric outer membrane and a reinforcing layer configured as a braided structure that is capable of changing its diameter. The sheath can be inserted into a patient in a first, smaller cross-sectional configuration, preferably over a small diameter dilator or tapered obturator. The obturator or tapered dilator is next removed and a hollow central dilator of large diameter is inserted into the interior lumen of the sheath. Upon insertion of the large diameter, hollow central dilator into the flexible shaft of the sheath, the sheath can expand diametrically to a second, larger, cross-sectional area, diameter, or radius. One or more catheters can be inserted therethrough to reach a target site within the vasculature. Following completion of the procedure, the central dilator can be removed resulting in elastomeric contraction of the outer membrane to a first, smaller cross-sectional area. The sheath can next be removed from the patient in its first, smaller, cross-sectional area configuration. The sheath can be configured using principles and design elements as described in U.S. Pat. No. 7,309,334 by Gerard von Hoffmann, titled "Intracranial Aspiration Catheter", the entirety of which is hereby incorporated herein by reference.

The reinforcement of the expandable regions can comprise wire, preferably malleable wire. The wire can have a round cross-section, a rectangular cross-section, a ribbon-like cross-section, or the like. The malleable wire can be bent by a dilator balloon, tapered dilator, hollow dilator, or the like, into the second, larger cross-section and the strength of the malleable wire can substantially overcome any resilient spring-back imparted by the polymeric component of the sheath wall.

In other embodiments, the wire can have elastomeric properties or shape memory properties. These embodiments can utilize shape-memory wire, pseudoelastic wire, superelastic wire, elastomeric wire, or the like. The wire can be nitinol, stainless steel, cobalt nickel alloy, or the like. The wire, in its shape-memory configuration can have an austenite finish temperature of around 25 to 35 degrees centigrade, preferably between 28 and 32 degrees centigrade so that body temperature blood causes the wire mesh to be biased to its larger, expanded configuration.

In another embodiment, the expandable region can comprise polymeric encapsulation of a braided or otherwise expandable shape memory reinforcing structure. The reinforcing elements or structure can have shape-memory characteristics. The sheath is inserted into the patient in its first, small cross-sectional area. The reinforcing elements are maintained below the martensite start temperature so that the reinforcing elements are substantially malleable, even at body temperature (approximately 37° C.). The sheath wall is next dilated with the balloon dilator as described herein. The dilator is next removed and the sheath becomes host to therapeutic or diagnostic catheters, which are inserted therethrough. Following removal of the catheters, electricity can be applied to lead wires at proximal end of the sheath. The electrical leads are operably connected to heaters in the vicinity of the reinforcing elements, or the electrical leads are operably connected to each end of the reinforcing elements. The electricity causes Ohmic or resistive heating of the reinforcing elements to above their austenite finish temperature. The reinforcing structure, having been shape-set in its small diameter configuration, returns to that small diameter configuration, bringing the entire expandable sheath wall down with it, to facilitate removal of the sheath from the patient. An austenite finish temperature of around 42° C. can be used in this application.

The dilator catheter can comprise an inner and outer member. The materials of the inner member and the outer member can comprise Hytrel, PEEK, composite, reinforced construction, polyester, polyurethane, polyethylene, or the like. The catheter hub can be fabricated from materials such as, but not limited to, polycarbonate, acrylonitrile butadiene styrene (ABS), polyurethane, polyvinyl chloride, and the like. The dilator balloon can be fabricated from stretch blow-molded polyester polyamide, polyamide, or polyester blends, using materials such as, for example, Eastman PET 9921 or similar.

In another embodiment, a coating is applied to the expandable areas to generate an inwardly biased, radially oriented contraction force. The expandable area can be forced to expand radially against the bias force of the coating. Once the radial expansion force is removed, the expandable area remains biased radially inward toward its smallest diameter, to which it will travel unless prevented from doing so.

The system can comprise radiopacity enhancements to improve visualization under fluoroscopy. Radiopaque markers can be affixed to the distal end of the sheath to denote its distal end, the extents of the expandable region or regions, or even the orientation of the sheath. The radiopaque markers can comprise bands or windings of metal such as, but not limited to, tantalum, platinum, platinum iridium, gold, and the like.

In certain embodiments of the sheath wall construction, an inner layer of polymer and an outer layer of polymer sandwich a reinforcing layer. The reinforcing layer can be a coil of metal such as, but not limited to, titanium, stainless steel, cobalt nickel alloy, nitinol, tantalum, and the like. The coil is preferably malleable, with little or no spring properties, and does not exhibit any elastomeric tendencies. The coil can be fabricated from flat wire with a thickness of 0.001 to 0.010 inches and preferably 0.002 to 0.005 inches. The width of the flat wire can range from 0.005 to 0.050 inches and preferably from 0.008 to 0.025 inches. The spacing between the coils can, for example range from substantially 0 to approximately 5 times the width of the coil wire. The coils can be fabricated from round stock, flat stock, or the like. The reinforcement can be sandwiched between the inner layer and the outer layer of polymeric material, wherein the inner and outer layers can be bonded or welded to each other through the space between the coils. The inner and outer polymeric layers can be fabricated from the same or different materials. Suitable materials for the inner and outer layers include, but are not limited to, polyurethane, silicone, Hytrel, PEEK, polyethylene, HDPE, LDPE, polyester, polyethylene blends, and the like. In yet another embodiment, a plastically deformable, malleable, or annealed, braid structure can also be used for reinforcement to beneficially eliminate the need for the malleable coil and permit a reduction in wall thickness while retaining the tensile strength and torqueability of the braid.

In certain embodiments, the sheath shaft can comprise multiple regions of varying flexibility along the axial length of the shaft. In some embodiments, the catheter shaft can have at least two regions of different flexibility. In other embodiments, the catheter shaft can comprise three or more (with a practical upper limit of six) regions of different flexibility. In yet other embodiments, the sheath shaft flexibility can be reduced toward the proximal end of the catheter and increased moving toward the distal end of the catheter. Moving from the proximal to the distal end of the catheter shaft, the flexibility of a given discreet section can be greater than the flexibility of the region just proximal and adjacent to said discreet section.

A sheath having a substantially collapsed, small diameter distal region can exhibit significantly increased flexibility in that area over its flexibility in non-expandable, or fully expanded, expandable regions. Such flexibility is especially useful when traversing tortuous or curved anatomy such as the aortic arch. Following such traverse, the sheath can be expanded to create a stiffer, larger diameter structure. Such construction is especially useful for the delivery catheter for an aortic valve which needs to approach the aortic root from its anatomically distal (downstream) aspect.

Another embodiment comprises a catheter configured to deliver a valve to the heart. In an embodiment, the delivery catheter for an aortic valve can be configured with an inner diameter ranging from about 14 French to about 32 French, with a preferred range of 18 French to 28 French. The length of the distal, expandable region should equal at least the arc length of the aortic arch and can range between 15 cm and 40 cm. The general construction of the aortic valve delivery catheter can be as described in U.S. Provisional Patent Application Ser. No. 60/674,226, filed Apr. 22, 2005, titled Expandable Trans-Septal Sheath, the entirety of which is hereby incorporated herein by reference. In other embodiments, an expandable delivery sheath can be used to deliver a catheter or a prosthesis to the heart through the subclavian artery. In these embodiments, the sheath working length can be generally shorter than the working length of an iliac access sheath. In this and all embodiments anticipated herein, the valve prosthesis replacement is delivered retrograde to the aortic valve root.

Another embodiment comprise method of use in which an expandable iliac sheath is provided in an aseptic, or sterile, package and is sterilized by ethylene oxide, gamma irradiation, electron beam irradiation, or the like. The patient is prepared in the standard hospital fashion for surgery and is appropriately draped. A percutaneous needlestick is made into the iliac arteries using the Seldinger technique described earlier in this document. A guidewire is advanced through the hollow 18-gauge needle and the needle is removed. The percutaneous access site can optionally be dilated with an Amplatz dilator or similar device at this time. The introducer sheath, in its first, small cross-sectional configuration, with its dilator is advanced over the guidewire and into the iliac artery where it is advanced into the abdominal aorta. The introducer sheath is next dilated to its second, larger cross-sectional configuration, using the pre-inserted dilator or by other suitable means. The dilator is next removed and any hemostasis valves are checked for closure at the proximal end of the sheath. Interventional catheters are next advanced through the expandable introducer sheath and toward their anatomical target. Following completion of the procedure, the interventional catheters are removed from the expandable iliac introducer sheath, again checking to ensure that there is no hemorrhage from the valves or ports at the proximal end of the sheath. The sheath is removed from the patient in one of three ways. In some embodiments, the sheath is simply withdrawn from the patient without collapsing the sheath. In some embodiments, the sheath is withdrawn from the patient without actively collapsing the sheath but the sheath collapses slightly following removal of the interventional catheters to ease withdrawal. In other embodiments, the sheath is actively reduced in diameter or cross-section and is then withdrawn from the patient. Hemostasis is maintained using standard hospital technique or by the application of a commercial percutaneous access hemorrhage control device.

The main reasons for the malleable embodiments include control over cross-sectional shape, ability to embed the reinforcement in the polymer layers without needing to create some difficult to manufacture decoupling of the polymer and the reinforcement, the high strength of the sheath following placement, and prevention of lumen re-collapse caused by body tissue. The ability of this device to remodel to the desired shape to generate a superhighway for placement of implants and other medical devices is superior to anything available today. Furthermore, the device provides a relatively smooth interior lumen which allows passage of instruments and implants of very large size without excessive binding or friction. No other sheath exists today that has these benefits.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 3A illustrates an expandable introducer sheath having three regions of expandability, in its radially collapsed configuration with its dilator catheter in place, according to an embodiment of the invention;

FIG. 3B illustrates the expandable introducer sheath of FIG. 1A in its radially expanded configuration and with the dilator catheter removed, according to an embodiment of the invention;

FIG. 4A illustrates a one-way expandable introducer sheath having a single area of expandability, in its first, unexpanded configuration with a dilator inserted therein, according to an embodiment of the invention;

FIG. 4B illustrates the one-way expandable introducer sheath of FIG. 1A in its expanded configuration with the dilator having been removed, according to an embodiment of the invention;

FIG. 4C illustrates a dilator capable of expanding the sheath, with the dilator balloon in its expanded configuration, according to an embodiment of the invention;

FIG. 5A illustrates a two-way expandable introducer sheath having a single area of expandability, in its first, unexpanded configuration, according to an embodiment of the invention;

FIG. 5B illustrates the two-way expandable introducer sheath of FIG. 3A in its second, expanded configuration, according to an embodiment of the invention;

FIG. 5C illustrates the two-way expandable introducer sheath of FIG. 3A following return to a third, actively collapsed configuration, according to an embodiment of the invention;

FIG. 6A illustrates an expandable introducer sheath and dilator, in its first, radially collapsed configuration, according to an embodiment of the invention;

FIG. 6B illustrates the expandable introducer sheath having been radially expanded and its dilator removed, according to an embodiment of the invention;

FIG. 6C illustrates the fully expanded introducer sheath with a prosthetic cardiac valve delivery catheter having advanced a prosthetic cardiac valve through the sheath, according to an embodiment of the invention;

DETAILED DESCRIPTION OF THE PREFERRED EMBODIMENTS

As used herein, the terms proximal and distal refer to directions or positions along a longitudinal axis of a catheter or medical instrument. Proximal refers to the end of the catheter or medical instrument closest to the operator, while distal refers to the end of the catheter or medical instrument closest to the patient. For example, a first point is proximal to a second point if it is closer to the operator end of the catheter or medical instrument than the second point. However, the terms anatomically proximal and anatomically distal refer to orientations within the body. A point is more anatomically distal if it is further from the heart than a point described as anatomically proximal.

Figure 1:
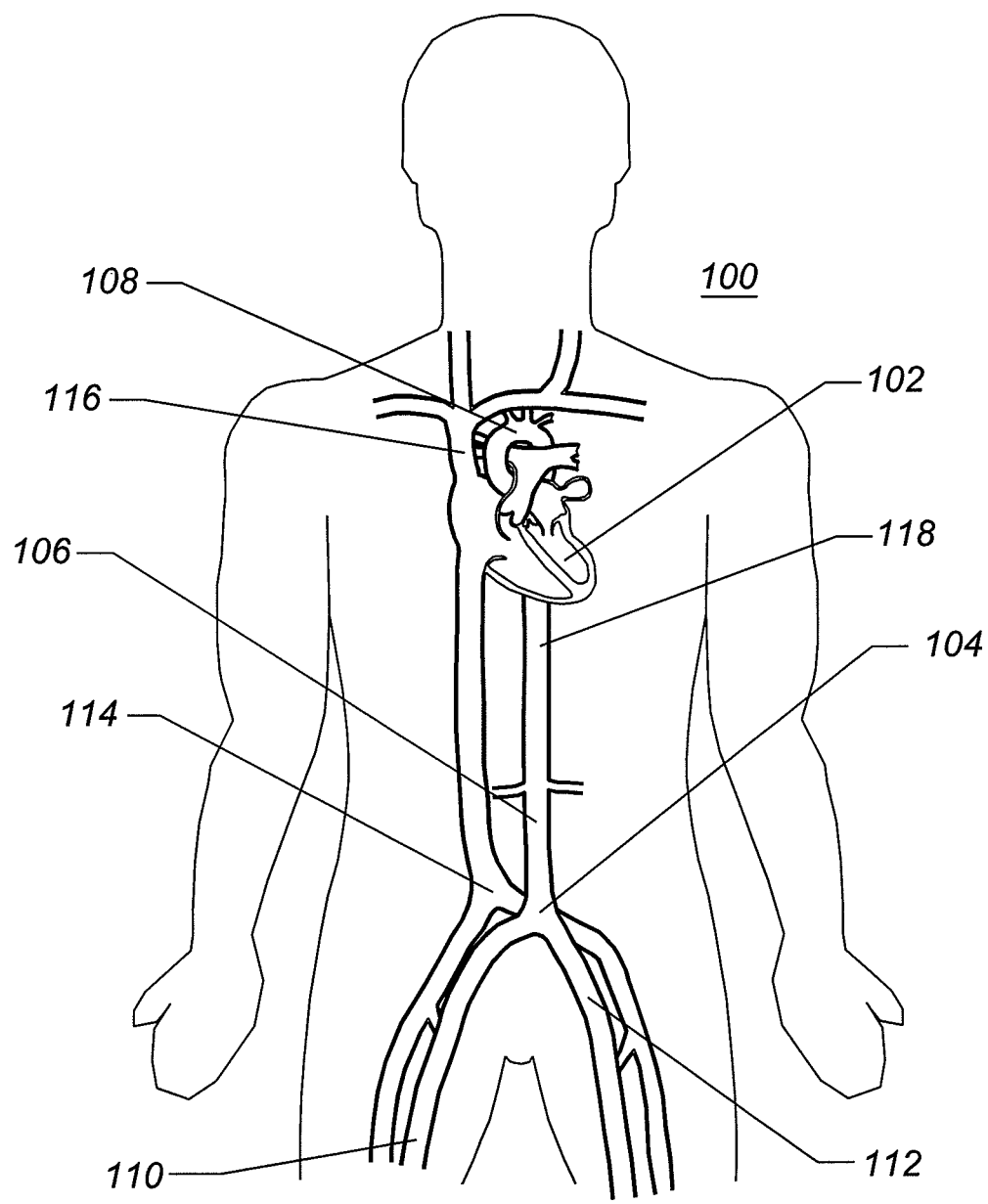
FIG. 1 is a front view schematic representation of the human circulatory system including the heart, the aorta, the iliac and femoral arteries, according to an embodiment of the invention.

FIG. 1 is a schematic frontal (anterior) illustration (looking posteriorly) of a human patient 100 that illustrates components of the central circulation. As shown, the central circulation generally comprises a heart 102, an aortic bifurcation 104, a descending aorta 106, an aortic arch 108, an inferior vena cava 114, a superior vena cava 116, an iliac artery 112, a femoral artery 110, and a thoracic aorta 11 8. In this illustration, the left anatomical side of the body of the patient 100 is toward the right of the illustration. FIG. 1 primarily illustrates components of the central circulation.

Referring to FIG. 1, the heart 102 is a pump, the outlet of which is the aorta, including the aortic arch 108, the thoracic aorta 118, the descending aorta 106, and the aortic bifurcation 104, which comprise the primary artery in the systemic circulation. The circulatory system, which is operably connected to the heart 102 further comprises the return, or venous, circulation. The venous circulation comprises the superior vena cava 116 and the inferior vena cava 114, which return blood from the upper extremities and lower extremities, respectively. The iliac arteries 112 are operably connected to, and receive blood from, the aortic bifurcation 104. The femoral arteries 110, are operably connected to, and receive blood from, the iliac arteries 112. The veins, which terminate in the superior vena cava 116 and the inferior vena cava 114, carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from left ventricle of the heart 102 to the tissues of the body 100. The pressures within the aorta undulate, with a modified triangle waveform, between diastolic pressures of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of about 300 mm Hg, or greater, can occur in extremely hypertensive persons.

Figure 2:
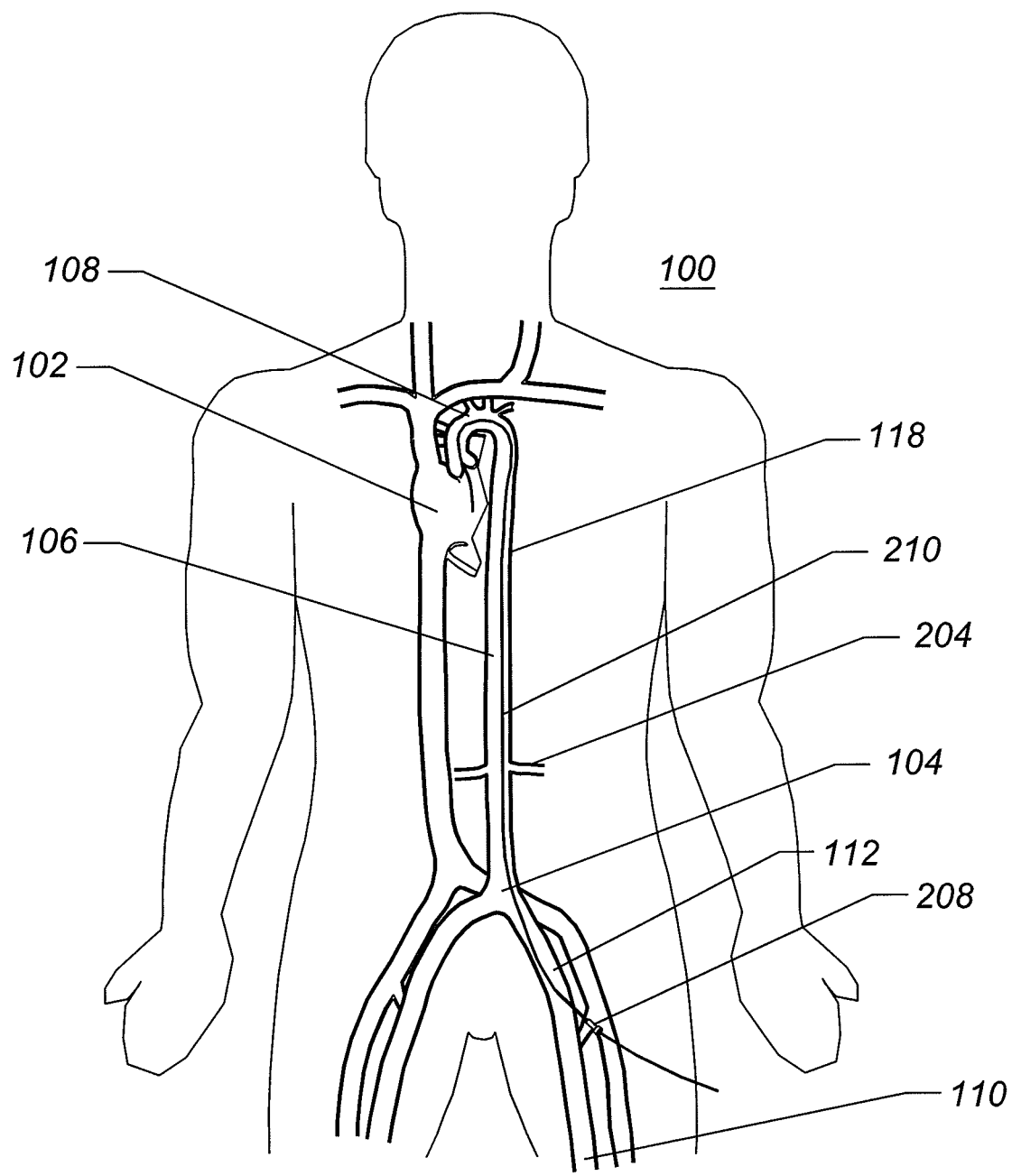
FIG. 2 is a front view schematic representation of the human circulatory system with a guidewire routed from the iliac artery into the aorta, according to an embodiment of the invention.

FIG. 2 is a schematic frontal illustration, looking posteriorly from the anterior side, of the patient 100. In this illustration, much of the right ventricle, left ventricle, and left atrium have been cut away to permit visibility of the thoracic aortic structure 118, which lies posterior to the heart 102. A hollow, 18-gauge needle 208 has been inserted into the left iliac artery 112 via a percutaneous puncture or incision. A guidewire 210 has been inserted through the hollow, 18 gauge needle 208 and routed, cranially, through the aortic bifurcation 104, up the descending aorta 106 past the renal arteries 204, through the thoracic aorta 118, and into the aortic arch 108. In this illustration, the left anatomical side of the patient 100 is toward the right. The guidewire 210 has been placed so that it can be used to track therapeutic or diagnostic catheters into a region of the thoracic aorta 118.

Referring to FIG. 2, the central arterial circulation, through which the guidewire 210 has been routed, may range from 60 to over 300 mm Hg depending on the level of hypertension or hypotension existent in the patient. By accessing the heart through the arterial circulation, the chance of hemorrhage from the catheter insertion site is minimized by use of hemostasis valves built into any catheters, sheaths, hollow needles, or introducers 208 used on the patient. The guidewire 210 is generally of sufficient length that the portion of it that extends outside the body. Thus, the guidewire is as long as, or longer than, twice the distance to the treatment site in the patient 100. The most commonly used guidewire diameter ranges from 0.032 inches to 0.038 inches or larger for these applications. Guidewires can be PTFE coated to improve lubricity and can have various types of tip configurations including, but not limited to, straight, "J", floppy tip, rigid tip, and the like. Access, in this illustration is gained through the iliac artery 112 but, if the catheters are small enough, the access can be gained through a femoral artery 110. As will be described in more detail below, in some embodiments, access can also be gained through the subclavian artery using a somewhat shorter device.

FIG. 3A illustrates one embodiment of an expandable iliac introduction sheath/dilator assembly 300. In the illustrated embodiment, the assembly 300 comprises three distinct regions of expandability distributed along the length of the sheath. As will be explained below, the assembly may have more or less distinct regions of expandability. In this arrangment, the sheath/dilator assembly 300 can comprise a sheath hub 302 further comprising a Tuohy-Borst type hemostasis valve 340 (or any other type of suitable hemostasis valve), a dilator hub 304, a proximal non-expandable tubing region 306, a first transition zone 308, a proximal expandable region 310, a central expandable region 312, a distal expandable region 314, a second transition zone 320, a third transition zone 322, a dilator balloon 318, and a length of dilator catheter tubing 316.

Referring to FIG. 3A, the sheath hub 302 can be coupled to the proximal end of the non-expandable tubing region 306. The distal end of the non-expandable tubing region can be coupled to the proximal end of the proximal expandable region 310 by the first transition zone 308. The distal end of the proximal expandable region 310 can be coupled to the central expandable region 312 by the second transition zone 320. The distal end of the central expandable region 312 can be coupled to the proximal end of the distal expandable region 314 by the third transition zone 322. The dilator balloon 422 (FIG. 4C) can be bonded, welded, or otherwise affixed to the dilator catheter tubing 316 by balloon bonds (not shown) at both ends of the dilator balloon 318. In one arrangement, the dilator balloon 422 is fully deflated and wrapped around the dilator catheter tubing 316 prior to insertion inside the sheath. The dilator hub 304 can be coupled to the proximal end of the dilator catheter tubing 316.

FIG. 3B illustrates the expandable introduction sheath 330 (in an expanded configuration), which is part of the sheath/dilator system 300 but with the dilator removed. The introduction sheath 330 comprises the sheath hub 302 further comprising the hemostasis valve 340, the proximal non-expandable tubing region 306, the first transition zone 308, the proximal expandable region 310, the central expandable region 312, the distal expandable region 314, the second transition zone 320, and the third transition zone 322.

Referring to FIG. 3B, the expandable introduction sheath 330 is illustrated with the proximal expandable region 310, the first transition zone 308, the second transition zone 320, the central expandable region 312, the third transition zone 322, and the distal expandable region 314 all having been expanded radially, or diametrically, to their second, larger cross-sectional configuration. Malleable reinforcing structures (not shown), which will be described in more detail below. within the first transition zone 308, the proximal expandable region 310, and the distal expandable region 314 maintain the sheath in its second, larger, cross-sectional configuration. Preferably, the malleable elements within the proximal expandable region 310 and the distal expandable region 314 maintain sufficient strength to overcome resilient forces exerted by the polymeric tubing within which the malleable elements are embedded, but insufficient strength to overcome the expansion forces of the dilator balloon 318 of FIG. 3A. The malleable reinforcing elements in the distal expandable region 314 can, in an embodiment provide similar strength as those reinforcing elements in the proximal expandable region 310. In other embodiments, the distal expandable region 314 can comprise reinforcing elements that are less strong than those in the proximal expandable region 310. The reinforcing elements can comprise structures such as, but not limited to, spiral windings of flat or round wire, braided elements of polymeric strands, wire, a mesh structure similar to a stent, a slotted tube with overlapping longitudinally oriented slots, or the like.

The dilator balloon 318 can be fabricated from PET, PETG, polyamide, polyamide, or the like, with wall thickness ranging between 0.001 to 0.006 inches, and can be capable of containing an internal pressure of 10 to 30 atmospheres, or higher. The dilator balloon 318 can be generally filled with incompressible fluid such as, but not limited to, saline, radiographic contrast media, or the like by the operator, through a balloon inflation port integral to, or affixed to, the dilator hub 304.

In a modified embodiment, the central expandable region 312 can comprise reinforcing elements similar to those used in the proximal expandable region 310 and the distal expandable region 314. In yet other embodiments, the central expandable region 312, and the distal expandable region 314 can comprise shape-memory reinforcing elements that can be heated or cooled to generate austenite or martensite conditions, respectively, that further can be used to drive the sheath wall from one cross-sectional configuration to another.

FIG. 4A illustrates an embodiment of an expandable iliac introducer sheath/dilator assembly 400 having only one region of expandability. The expandable region 408 and the transition zone 406 are illustrated in their first, smaller cross-sectional configuration. The transition zone 406 forms a taper between the diametrically collapsed expandable region 408 and the larger proximal non-expandable region 404. The introducer sheath/dilator assembly 400 of the illustrated embodiment comprises a sheath hub 402, a length of proximal non-expandable tubing 404, a transition zone 406, an expandable region 408, the dilator balloon 318, the length of dilator tubing 316, and the dilator hub 304.

Referring to FIG. 4A, the sheath hub 402 can be coupled to the proximal end of the proximal non-expandable tubing 404. The distal end of the proximal non-expandable tubing 404 can be coupled to the proximal end of the expandable region 408 by the transition zone 406. The dilator hub 304, dilator tubing 316, and dilator balloon 422 (FIG. 4C) can be assembled as described in FIG. 3A.

FIG. 4B illustrates the expandable introduction sheath 430, which is part of the sheath/dilator system 400 but with the dilator removed. The expandable region 408 and the transition zone 406 have been fully expanded to their second, larger, cross-sectional configuration. The introduction sheath 430 comprises the sheath hub 402, the proximal non-expandable tubing region 404, the first transition zone 406, and the expandable region 408.

FIG. 4C illustrates a sheath dilator 400 comprising a dilator shaft 420, the dilator hub 304, the dilator balloon 422, the distal fairing 318, and the sheath distal tubing 316. The dilator balloon 422 comprises neck down regions and the dilator balloon is affixed to the dilator shaft 420 or the dilator hub 304 at the proximal neck down region and to the sheath distal tubing 316 at the distal neck down region using adhesives, welding, or a combination thereof. The dilator balloon 422 can be an angioplasty type balloon fabricated from material such as, but not limited to, PET, polyimide, polyamide, reinforced polymers, or the like. The dilator balloon 422 can be configured to generate pressures ranging up to 25 or 30 atmospheres when filled with pressurized liquids such as, but not limited to, radiopaque dye contrast media, saline, Ringer's lactate, and the like. The dilator balloon 422 comprises a flat length at least as long as the combined length of the sheath expandable distal region 408 and the transition zone 406, and is preferably somewhat longer to facilitate manufacturability and reliability. The dilator balloon 422 can comprise an inflated diameter approximately equal to or slightly greater than that of the fully expanded distal region 408 of the sheath. The balloon 422 can comprise wall thicknesses ranging from 0.0005 to 0.005 inches and preferably ranging between 0.0007 and 0.002 inches. Note that the distal fairing 318, which is beneficially fabricated from soft elastomeric materials expands and folds distally off the shoulders of the balloon 422 such that when the balloon 422 is deflated, the fairing 318 returns to a small diameter that can be withdrawn proximally through the lumen of the sheath 430.

FIG. 5A illustrates an embodiment of a two-way expandable sheath dilator assembly 500 capable of being radially expanded and then radially constricted prior to removal from the patient. The sheath dilator assembly 500 comprises the dilator hub 304, the dilator balloon 422, the length of dilator tubing 316, the sheath hub 502, the proximal sheath tubing 504, the transition zone 506, and the expandable sheath region 508.

Referring to FIG. 5A, the sheath hub 502 can be coupled to the proximal end of the proximal sheath tubing 504. The distal end of the proximal sheath tubing 504 can be coupled to the proximal end of the expandable region 508 by the transition zone 506. The dilator hub 304, dilator tubing 316, and dilator balloon 318 can be assembled as described in FIG. 3A.

The expandable region 508, in the illustrated embodiment, can comprise shape memory elements (not shown) fabricated from nitinol, which is configured with an austenite finish temperature in excess of body temperature (normally around 37 degrees centigrade). Thus, the expandable region 508 can be heated by application of electricity to generate resistive heating and temperature increase to above the austenite finish temperature. A suitable austenite finish temperature can range from 38 to 50 degrees centigrade. Such heating can be performed at the conclusion of the procedure, following removal of any therapeutic or diagnostic instruments from the center of the sheath. The sheath will generally be within the blood stream and not touching any vascular walls. Furthermore, flowing blood can disperse heat generated by the resistive heating elements so as to minimize localized heating damage effects to the body. The shape memory elements can be heat set to a collapsed, small diameter configuration to which they will be biased following application of resistive heating. The reinforcing structures can be configured as a braid, a spiral winding, a woven mesh, a slotted tube, or the like. The reinforcing structures can be heat set in a collapsed, or small, initial diameter configuration and then be cooled to below martensite finish temperature, at which point the reinforcing structures can be expanded for coating with a polymer or other suitable manufacturing process.

FIG. 5B illustrates the two-way expandable sheath dilator assembly 500 with the dilator balloon 318 fully inflated to expand the sheath radially, or diametrically, outward. The dilator balloon 318 runs the entire length and slightly beyond the extents of the expandable region 508. The sheath dilator assembly 500 further comprises the expandable region 508, the transition zone 506, the proximal non-expandable sheath tubing 504, the sheath hub 502, and the length of dilator tubing 316.

FIG. 5C illustrates a two-way expandable sheath 530, which is the sheath/dilator assembly 500 following removal of the dilator. The two-way expandable sheath 530 comprises the proximal tubing 504, the hub 502, the transition zone 506, and the expandable region 508. The expandable region 508 is illustrated radially collapsed following removal of the balloon dilator.

Referring to FIG. 5C, the expandable region 508 is re-collapsed to its third, smaller cross-sectional configuration by application of heat to the shape-memory reinforcement embedded within the expandable region. The expandable region 508 can be made to uniformly compress to a smaller diameter, or it can be made to fold into any of a variety of cross-sectional patterns exhibited by a tube that is folded along longitudinally disposed folds. In the embodiments where uniform reduction in cross-sectional shape is imparted, the reinforcement can comprise a braid that elongates longitudinally when it reduces its diameter. The polymeric surround of the expandable region 508 is preferably elastomeric and comprises materials such as, but not limited to, polyurethane, thermoplastic elastomer, silicone elastomer, and the like. The interior of the wall of the expandable region is advantageously coated with a layer of high lubricity and low friction to facilitate catheter or device introduction therethrough without hang-up.

In another embodiment, the expandable region 508 can be maintained with an open inner lumen if a hollow sleeve or dilator (not shown) is inserted therethrough, or if the expandable region 508 has at least some hoop strength gained by appropriate wall design or reinforcement within the wall. Referring to FIG. 5C, the hollow sleeve or dilator (not shown) can comprise a hollow axially elongate tube with a proximal end and a distal end. The tube can comprise structures and materials that impart flexibility to the hollow sleeve or dilator but the tube advantageously comprises the properties of column strength and kink-resistance. The proximal end of the tube comprising the hollow sleeve or dilator can be affixed to a sleeve hub. The structure of the tube comprised by the hollow sleeve or dilator is preferably very thin and can further comprise a single material, preferably polymeric, or it can comprise a built-up, composite structure with a reinforcing layer and a polymeric surround. The reinforcing layer can comprise a braid, weave, helical coil, slotted tube, or the like. In a preferred embodiment, the hollow sleeve or dilator tube can comprise polymeric surround materials such as, but not limited to, polyamide, polyamide, polyurethane, polyester, polyether ether ketone, Hytrel, or the like. The length of the hollow sleeve or dilator tube is sufficient to extend from the proximal end of the sheath hub 502 to the distal end of the expandable region 508. The distal end of the hollow sleeve or dilator tube can comprise a bevel on its outer surface to assist with coercing the sheath expandable region 508 to expand from its first, smaller cross-sectional area to its second, larger cross-sectional area. The distal end of the hollow sleeve or dilator tube can further comprise shape-memory elements that are bent radially inward at the distal end in their martensitic phase and then, upon exposure to body temperature blood, they expand radially outward to form a straight, non-inwardly beveled distal end. In yet another embodiment, an obturator is provided which closely fits the inside diameter of the hollow sleeve or dilator tube and which comprises a tapered distal end suitable for advancement into a body lumen, vessel, or expandable sheath tube. The hollow sleeve or dilator tube is advanced into the expandable sheath as a unit. The obturator can comprise a hub at its proximal end that releasably snaps or connects to the distal end of the hollow sleeve or dilator tube hub. Once the composite structure is advanced completely into the expandable sheath, the obturator can be removed revealing the large central lumen suitable for the introduction of catheters, instruments, implants, and the like.

FIG. 6A illustrates an embodiment of the iliac sheath system 600 comprising a dilator 400 further comprising a distal fairing 318, a main dilator tube 330, an optional outer dilator tube (not shown), a dilator balloon 422, a dilator hub 304 further comprising an inflation port 332, and a sheath 630 further comprising a proximal sheath tube 604, a transition zone 606, a distal sheath tube 608, and a sheath hub 602. A guidewire 210 is slidably disposed within an inner lumen of the dilator 400.

Referring to FIG. 6A, the distal fairing 318 can be coupled to the main shaft 330 of the dilator 400 near its distal end. The distal fairing 318 can be fabricated from elastomeric materials such as, but not limited to, thermoplastic elastomer, silicone elastomer, polyurethane elastomer, Hytrel elastomer, and the like. A balloon (not shown) can reside with its flat length disposed along at least the entire distal sheath tube 608 and the transition zone 606. The balloon (not shown) can be coupled to the main shaft 330 of the dilator 400 and the interior of the balloon (not shown) is operably connected to an annulus running between the main shaft 330 and F an external shaft (not shown) or within a lumen of the main shaft 330. The annulus (not shown) or lumen (not shown) operably extend between the inflation port 332 and a skive, scythe, or port opening into the interior of the balloon (not shown). The balloon (not shown) is preferably an angioplasty-type non-elastomeric balloon fabricated from material such as, but not limited to, PET, PET copolymers, polyamide, polyimide, reinforced polymers, and the like. The balloon (not shown) has a wall thickness that can range between approximately 0.0004 and 0.005 inches, and preferably between 0.001 and 0.002 inches. The ends of the balloon (not shown) are tapered inward to form shoulders (not shown) that are bonded, welded, or otherwise affixed to the main shaft 330 at the distal end and either the main shaft 330 or an external shaft (not shown) at the proximal end. The dilator hub 304 can comprise an inflation port 332 that is operably connected to the inflation lumen or annulus of the dilator 400. In another embodiment, the proximal end of the dilator balloon 422 (FIG. 4C) can extend proximally all the way to the dilator sidearm or hub 304. In this embodiment, fluid pressure applied to an inflation port on the dilator hub 304 is operably connected to the annulus between the dilator balloon 422 and the catheter shaft, allowing balloon inflation fluid such as radiopaque dye contrast media, saline, or the like to be routed into the balloon internal structure and causing the balloon to forcibly expand diametrically. This arrangement can result in a beneficial increase in rated balloon burst, or inflation, pressure. Rated balloon burst pressures in excess of about 25 to 30 atmospheres can be achieved with 99.9% reliability and 95% confidence.

The dilator 400 (FIG. 4C) is slidably disposed within the central lumen of the sheath 630 and further comprises an expandable dilator (not shown) such as, but not limited to, an angioplasty type balloon, malecot, reverse collet, or other device capable of expansion to approximately 0.2-mm (0.5 French), or greater, larger than the diameter of the sheath. The balloon (not shown) can be inflated through the inflation lumen within the catheter shaft, which is operably connected, at its proximal end, to a dilator hub or inflation port. Following inflation, which expands the distal end of the sheath, the dilator expansion element, such as the balloon (not shown), can be deflated or collapsed, following which it can be removed from the sheath 630 along with the nose cone 318.

The sheath hub 602 preferably comprises ports that further comprise, or are terminated by, hemostasis valves. The hemostasis valves are configured to prevent hemorrhage from, or air intake into, the lumen of the sheath 630. The hemostasis valves can comprise between one and 5 elements to form a seal against nothing inserted into the valve, form a seal against a maximum diameter object inserted through the valve, and form a seal against anything of intermediate size inserted through the valve. The hemostasis valve elements can be fabricated from soft silicone or other elastomer. The hemostasis valve elements can be coated or impregnated with lubricious coatings such as silicone oil or hydrophilic layer. The hemostasis valve elements can comprise duckbill valves, pinhole valves, slit valves, X-slit valves, ring seals, and the like.

The distal sheath tubing 608 is folded longitudinally in a carefully predetermined pattern comprising between one and four exterior fold edges, wherein the folds extend all the way from the proximal end of the transition zone 606 to the distal end of the distal sheath tube 608. The distal fairing 318 is configured to cover the distal exposed edge of the distal sheath tube 608 to provide a smooth taper against which the sheath system 600 can be advanced into the vasculature.

FIG. 6B illustrates the iliac sheath 630 following expansion of the distal region 608 and removal of the dilator 400 and the guidewire 316 of FIG. 6A. The proximal sheath tube 604, which is affixed at its proximal end to the sheath hub 602, can comprise one or two layers of mesh reinforcement 612 and a spring-coil reinforcement 610. The distal sheath tube 608 and the transition zone 606 can further comprise a malleable coil 614 and, optionally, the mesh reinforcement 612. The entire sheath tube, which comprises a central lumen (not shown), comprises an approximately constant inner diameter along its entire length. The approximately constant diameter is beneficial in that objects of large diameter can be inserted and advanced completely from the proximal end and out the distal end of the sheath 630. The sheath 630 is illustrated in partial breakaway view to show the coil reinforcement layers 610 and 614 along with the mesh 610.

In one embodiment, an inner sheath layer 634 is first laid down over a PTFE-coated stainless steel mandrel (not shown). The sheath inner layer 634 can be preferably fabricated from lubricious materials such as, but not limited to, polyethylene, HDPE, LDPE, blends of HDPE and LDPE, PTFE, FEP, PFA, Hytrel, Pebax, or the like. The sheath inner layer 634 can also be coated, on its inner surface, with friction retarding materials such as, but not limited to, silicone oil, polyurethane-based hydrophilic slip coating materials, and the like. The optional mesh layer 612 is next applied over the inner layer 634. The coil reinforcement layers 610 and 614 can next be applied over the mesh 612. In other embodiments, a second layer of mesh can optionally be applied over the coil 614. The second layer of mesh can have different properties from the inner layer of mesh, including different filament diameter, filament count, number of picks, and filament density or angle. Finally, an outer layer 632 of polymeric material can be applied over the reinforcement, after which shrink tubing can be placed around the entire structure and heated to shrink, melt, fuse, and bond the inner layer to the outer layer while sandwiching the reinforcing layers therebetween. The sheath inner layer 634 can have a wall thickness ranging between about 0.001 and 0.010 inches with a preferred range of about 0.002 and 0.006 inches. The sheath outer layer 632 can have a wall thickness ranging between about 0.001 and 0.010 inches with a preferred range of about 0.001 to 0.006 inches.

The mesh 612 can be formed from a braid, weave, knit or other structure formed into a tubular cross-section. The mesh 612 can be fabricated from flat or round strands. The mesh 612 can be fabricated from polymers such as, but not limited to, polyethylene naphthalate (PEN), PET, polyamide, polyimide, or the like. The mesh 612 can also be fabricated from metals such as, but not limited to, malleable stainless steel, spring stainless steel, nitinol, titanium, cobalt nickel alloy, tantalum, gold, platinum, platinum alloy, and the like. The lateral size of the strands of the mesh 612 can range between 0.001 and 0.010 inches in at least one dimension. The number of ends of the mesh can range between 2 and 50.

The construction of the distal sheath tube 608 can comprise a coil of wire 614 with a wire diameter of 0.001 to 0.040 inches in diameter and preferably between 0.002 and 0.010 inches in diameter. The coil 614 can also comprise a ribbon wire or a flat wire that is 0.001 to 0.010 inches in one dimension and 0.004 to 0.040 inches in the other dimension. Preferably, the flat wire is 0.001 to 0.005 inches in the small dimension, generally oriented in the radial direction of the coil, and 0.005 to 0.020 inches in width, oriented perpendicular to the radial direction of the coil. The pitch of the coil 614, which is related to the spacing between coil turns can range from about 0 to about 5 times the ribbon width or wire diameter. Preferably, some space exists between the coil turns to permit bonding between the outer layer 632 and the inner layer 634 so a preferred spacing is between 0.5 and 4 times the width of the ribbon. The outer layer 632 of polymeric material can have a wall thickness of 0.001 to 0.020 inches and the inner layer 614 has a wall thickness of between 0.001 and 0.010 inches. The wire used to fabricate the coil 614 can be fabricated from annealed materials such as, but not limited to, gold, stainless steel, titanium, tantalum, nickel-titanium alloy, cobalt nickel alloy, and the like. The wire is preferably fully annealed. The wires can also comprise polymers or non-metallic materials such as, but not limited to, PET, PEN, polyamide, polycarbonate, glass-filled polycarbonate, carbon fibers, or the like. The wires of the coil reinforcement can be advantageously coated with materials that have increased radiopacity to allow for improved visibility under fluoroscopy or X-ray visualization. The radiopaque coatings for the coil reinforcement may comprise gold, platinum, tantalum, platinum-iridium, and the like. The mechanical properties of the coil are such that it is able to control the configuration of the fused inner layer 634 and the outer layer 632.

When the distal region 608 is folded (see description below with reference to FIGS. 14A and 14B) to form a small diameter, the polymeric layers 634, 632, which can have some memory, do not generate significant or substantial springback. The sheath wall is preferably thin so that it any forces it imparts to the tubular structure are exceeded by those forces exerted by the malleable distal reinforcing layers 614, 632. Additionally, a peel away, slide away, or otherwise removable protective sleeve (not shown) is useful but not necessary to maintain the collapsed sheath configuration.

FIG. 6C illustrates the sheath 630 having been expanded diametrically in a prior step, with a prosthetic heart valve delivery catheter 622 shaft inserted therethrough. A prosthetic heart valve 620 is affixed to the delivery catheter shaft 622 near or at the distal end of the catheter shaft 622. The delivery catheter shaft 622 further comprises a hub 624, which is affixed to the proximal end of the delivery catheter shaft 622, and a balloon inflation sidearm port 626. The central port, at the proximal end of the hub, is preferably terminated by, or comprises, a hemostasis valve. The hemostasis valve is configured to prevent hemorrhage from, or air intake into, the valve delivery catheter.

It should be appreciated that modifications thereof can be used to provide an expandable region of the catheter with an initial small cross-sectional diameter. By unfolding the distal region 1400, the diameter of the distal region can be increased to a larger diameter. In the smaller folded configuration, the malleable structures described above can maintain the distal region in the smaller folded configuration. In other embodiments, an external structure can maintain the sheath in the folded configuration. In this smaller folder configuration it has been noted that the flexibility of the catheter (e.g., the ability of the catheter to navigate the aortic arch) is increased. When the catheter is unfolded and expanded, the malleable structure can reform to the larger unfolded diameter and to the shape of the anatomy (e.g., the aortic arch) in which the sheath his placed. In the unfolded configuration, the malleable structures provide hoop strength maintain the patency of the lumen.

In other embodiments, the exterior of the sheath, and optionally the internal lumen of the sheath, can be coated with a lubricious coating comprising materials such as, but not limited to, silicone oil or a hydrophilic hydrogel comprising polyethylene glycol, polyether polyurethane, or the like. Other coatings can include antimicrobial coatings such as those fabricated from silver azide or anticoagulant coatings such as those comprising heparin.

In the illustrated embodiment, The prosthetic valve delivery catheter 622 is configured to deliver the collapsed prosthetic valve 620 to an implantation site within the patient. Typical valves include aortic and mitral valve replacements. The prosthetic valve 620 further comprises an expandable stent support and fixation elements. The valving element is suspended within, or around, the expandable stent and can comprise between one and four leaflets fabricated from polyurethane, cross-linked pericardium, fixed natural porcine aortic roots, or homografts. The outside diameter of the collapsed prosthetic valve 620 is such that the valve 620 can be slidably advanced through the lumen of the sheath 630. In other embodiments, the valve delivery catheter can comprise an external sleeve to retain the valve 620 in its smallest possible diameter during placement into the patient. The expandable stent support can be malleable and balloon expandable, self-expanding, or self expanding with balloon expansion augmentation.

Figure 7:
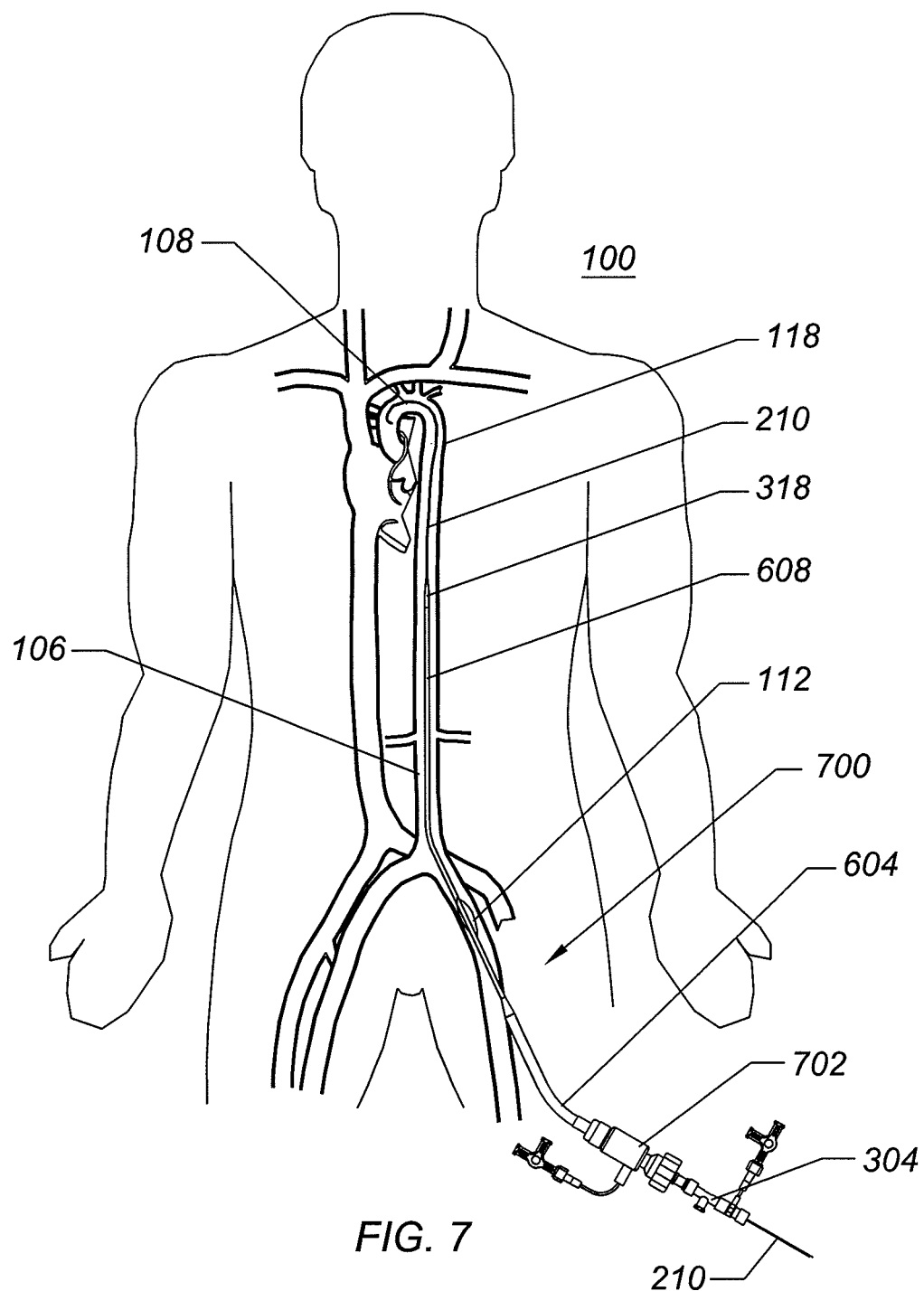
FIG. 7 illustrates an expandable introducer sheath advanced into the iliac artery of a patient in its first, radially collapsed configuration, according to an embodiment of the invention.

FIG. 7 illustrates an expandable iliac sheath 700 having been inserted into the femoral artery 112 of a patient 100. The expandable iliac sheath 700 comprises the proximal sheath tube 604, the distal sheath tube 608, the sheath hub 702, a dilator further comprising a dilator hub 304, the dilator nose fairing 318, and a guidewire 210: The patient 100 further comprises the descending aorta 106, and the aortic arch 108.

Figure 8:
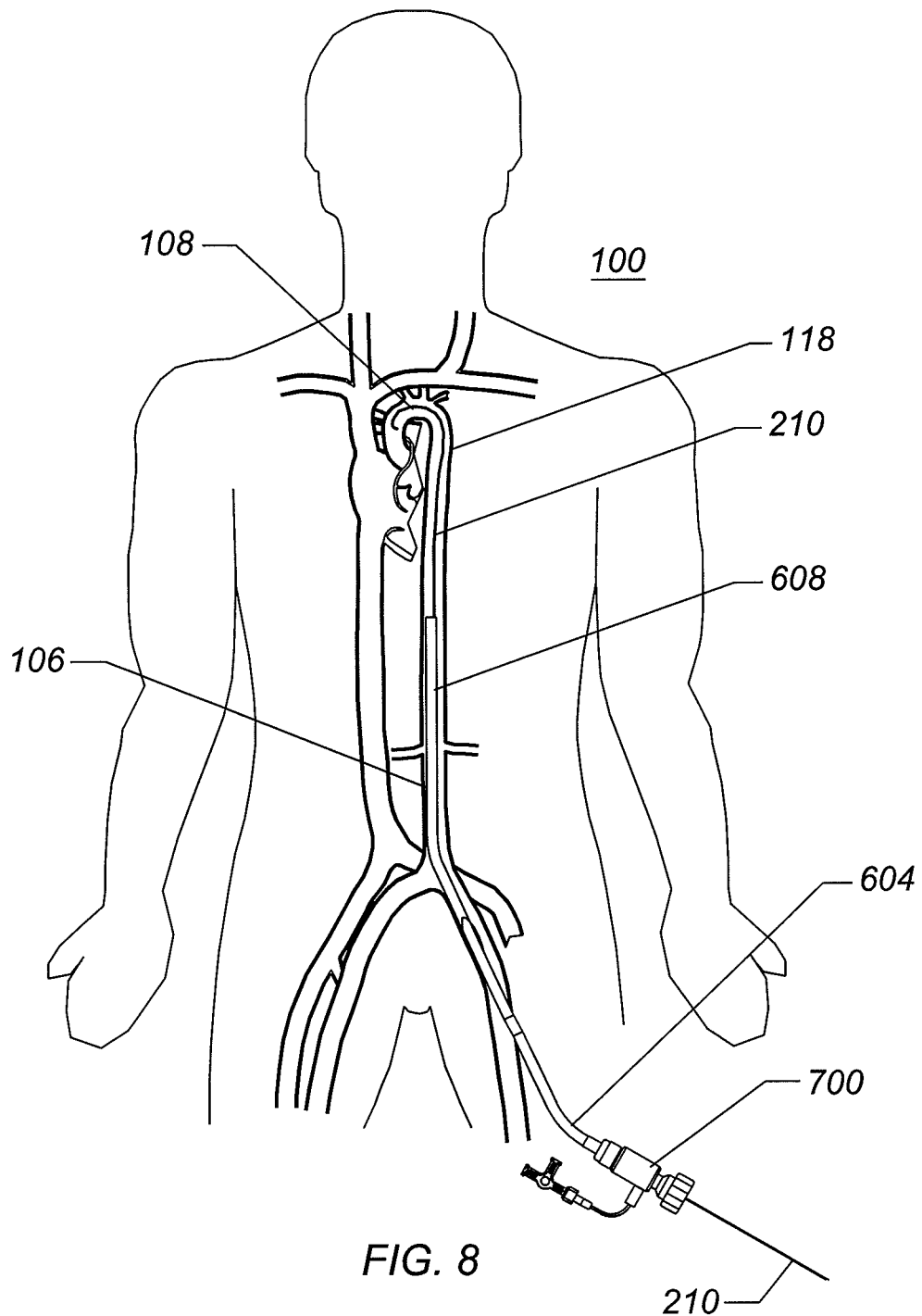
FIG. 8 illustrates an expandable introducer sheath having been dilated within the iliac artery of a patient, according to an embodiment of the invention.

Referring to FIG. 7, the sheath hub 702 is a single lumen hub with a large hemostasis valve and a purge port. The sheath hub 702 can be to the proximal end of the proximal sheath tubing 604. In the illustrated embodiment, the distal end of the distal sheath tube 608 has been advanced at least past the aortic bifurcation and can be advanced as far as across the aortic arch 108 and just downstream of, or through, the aortic valve. The distal sheath tube 608 and the dilator expandable component (not shown), compressed within the distal sheath tube 608 are in their first, small diameter configuration to permit maximum flexibility and minimum profile, for negotiating the vasculature, FIG. 8 illustrates the expandable iliac sheath 700 having had its distal tubing 608 diametrically expanded by the dilator, which has been removed to reveal the large, through working lumen. The expandable iliac sheath 700 comprises the proximal sheath tube 604, the now dilated distal sheath tube 608, and a guidewire 210. The patient 100 further comprises the thoracic aorta 118, the descending aorta 106, and the aortic arch 108.

Referring to FIG. 8, the guidewire 210 can remain in place and can be withdrawn at this time, if appropriate to the procedure. The expanded sheath can be inserted as shown or can be beneficially advanced so that its distal end is just downstream of the aortic valve.

Figure 9:
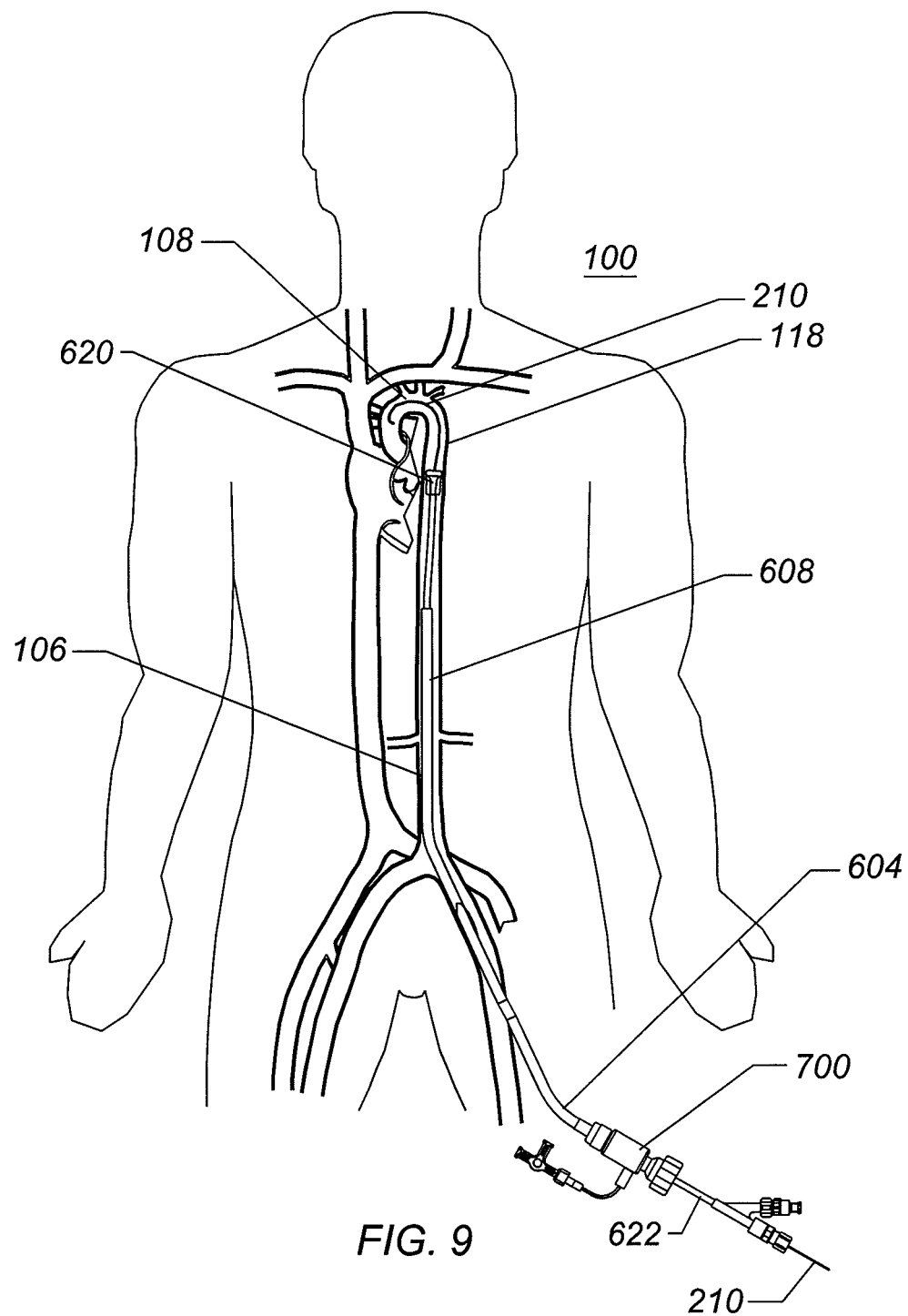
FIG. 9 illustrates a prosthetic aortic valve delivery catheter advanced through the expanded introducer sheath of FIG. 5, according to an embodiment of the invention.

FIG. 9 illustrates the expandable iliac sheath 700 with an aortic valve delivery catheter 622 and prosthetic aortic valve 620 having been advanced therethrough. The guidewire 210 can remain in place but can be removed, if desired. The prosthetic aortic valve 620 is being advanced toward the natural aortic root (not shown) 1022 and will be implanted therein.

Figure 12:
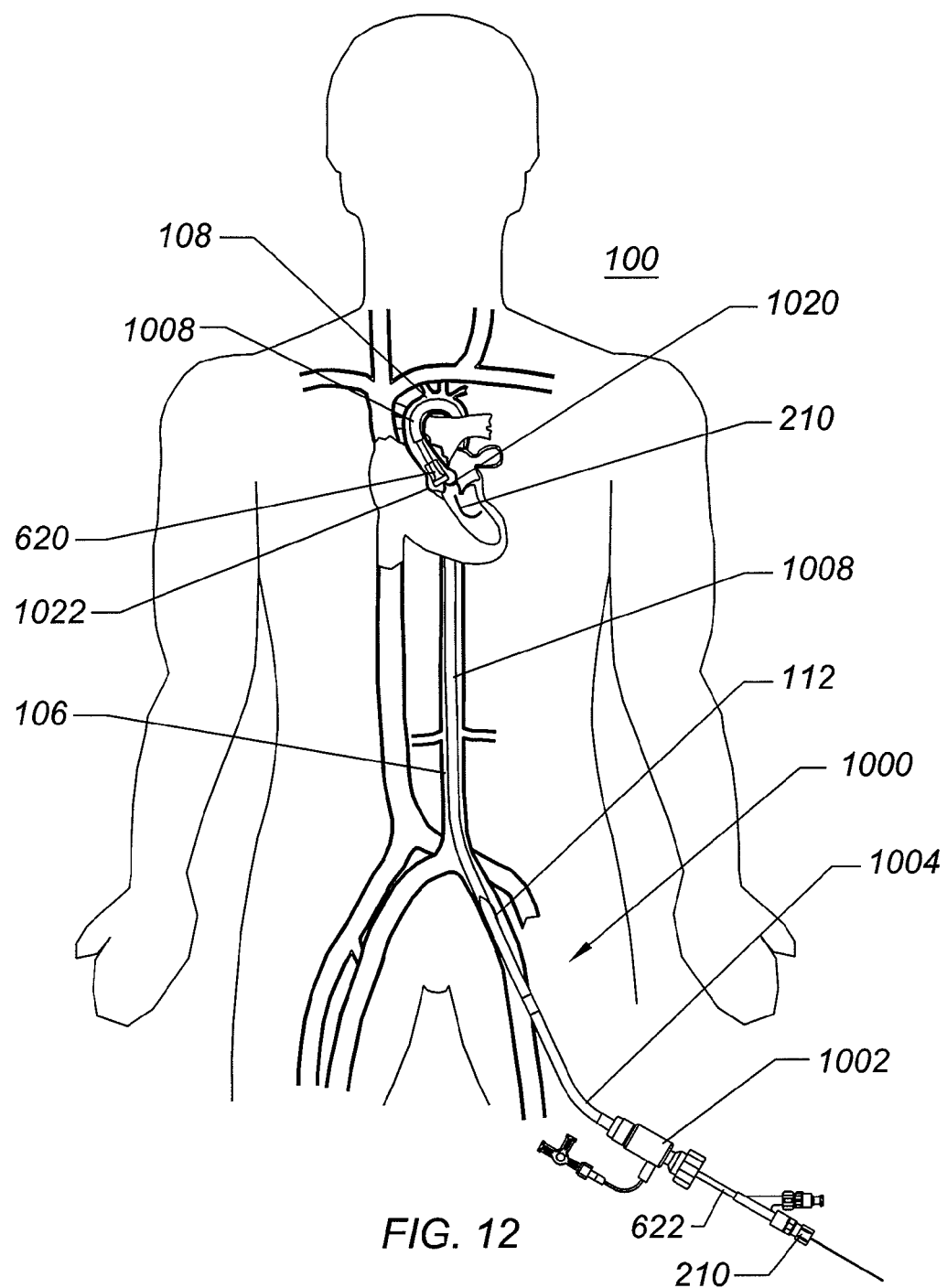
FIG. 12 illustrates a prosthetic aortic heart valve replacement being placed through the sheath by means of a catheter introducer, according to an embodiment of the invention.

FIG. 9 FIG. 12 illustrate an embodiment in which the distal end of the sheath is shown in the thoracic aorta 118 but is beneficially located in the aortic arch 108 or proximate the aortic valve root 1022 for ease of delivery of the aortic valve prosthesis 620. The aortic valve delivery catheter 622 can comprise a dilatation balloon to expand the aortic valve prosthesis 620, dilate the diseased natural aortic root 1022, and firmly implant the prosthesis 620 within the natural diseased aortic root 1022. Following implantation of the prosthesis 620, a release mechanism comprised by the catheter 622 is activated to detach the prosthesis 620 so the catheter 622 and the sheath 700 can be removed from the patient. A hemostasis sheath (not shown) can be advanced into the incision in the iliac artery to minimize loss of blood and stabilize the patient during the immediate postoperative period. The hemostasis sheath (not shown) can comprise a catheter tube approximating the diameter of the proximal sheath tubing 604 along with a hemostasis valve to prevent unwanted blood loss.

The hemostasis sheath (not shown) the guidewire 210, and the sheath 700 can be provided in a kit, or packaged together for the convenience of the user. All components can be sterilized using ethylene oxide or radiation sterilization, the latter at dosages of, for example, about 25 to 40 kGray. The components of the kit can be packaged in a single aseptic or double aseptic packaging system.

Figure 10:
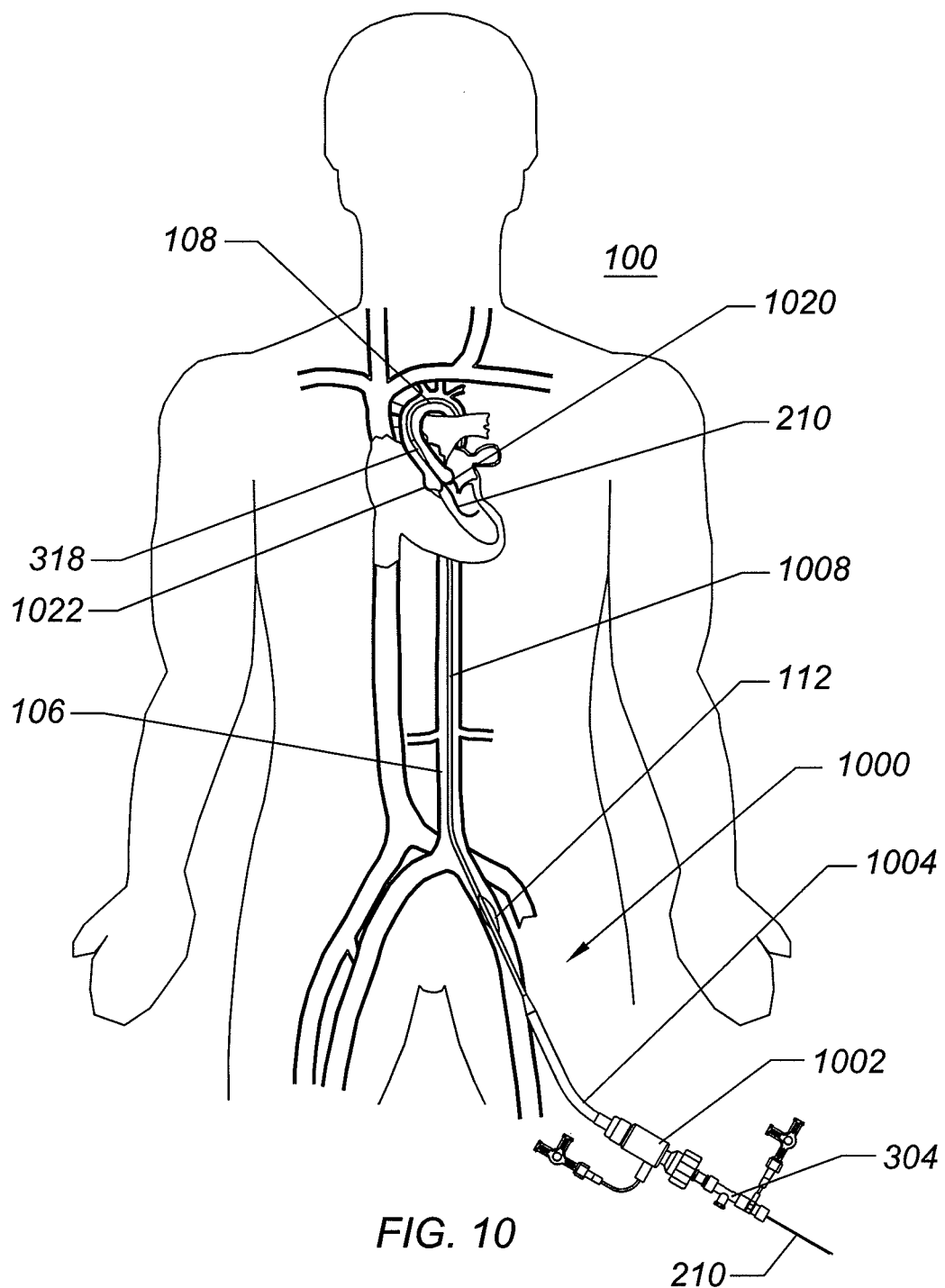
FIG. 10 illustrates a diametrically collapsed aortic sheath inserted into an iliac artery and then routed around the aortic arch and positioned within the aortic root, according to an embodiment of the invention.

FIG. 10 illustrates an aortic sheath 1000 inserted into an iliac artery and then routed, in its first, with its expandable distal end 1008 in its diametrically collapsed configuration, around the aortic arch 108 and positioned just distal to the aortic valve 1020. The natural aortic valve 1020 is situated within the aortic root 1022, the aortic root 1022 further comprising three sinus of Valsalva. The heart is illustrated in partial cross-section. The guidewire 210 extends through the aortic valve 1020 and into the left ventricle.

Referring to FIG. 10, the aortic sheath 1000 is configured to reach from a femoral or iliac 112 access site to the left ventricle of the heart. The proximal non-expandable region 1004 can be maintained in position outside the patient 100 or it can be inserted into the femoral or iliac artery. The small diameter of the distal expandable region 1008 results in a highly flexible configuration that is resistant to kinking because its internal lumen is filled with dilator. This configuration can be routed around the aortic arch much more easily than another catheter having a larger diameter, similar to that of the proximal region of the catheter. The distal fairing, or nose cone 318, which is affixed to the dilator, is situated just distal to the aortic valve.

Figure 11:
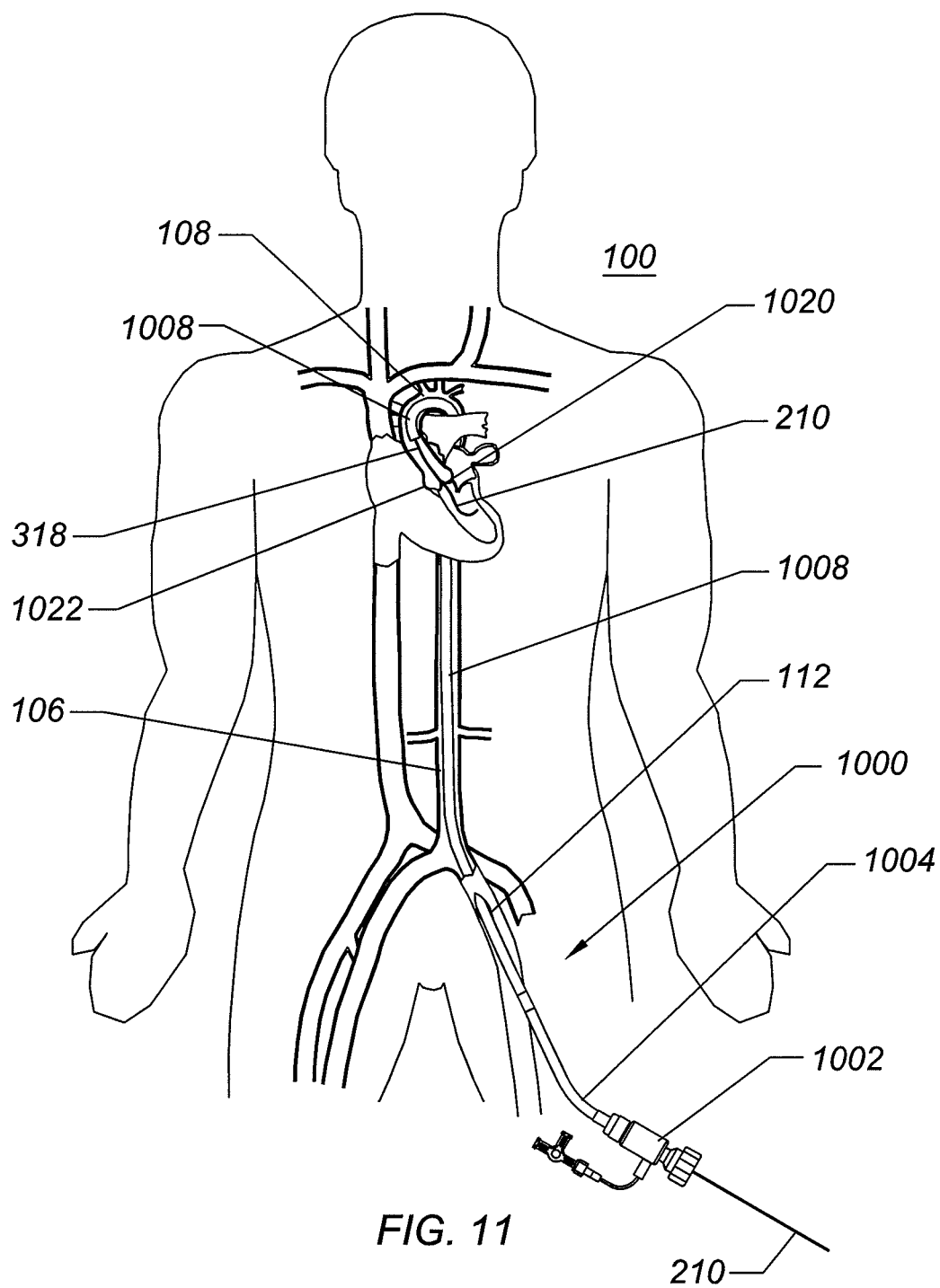
FIG. 11 illustrates an aortic sheath which has had its expandable distal region expanded by the dilator, following which the dilator has been removed, according to an embodiment of the invention.

FIG. 11 illustrates the patient 100 wherein the sheath 1000 has had its expandable distal region 1008 expanded by the dilator system, following which the dilator system 400 (Refer to FIG. 4C), further comprising the dilator hub 304, has been removed. The central lumen (not shown) of the sheath 1000 comprises a relatively large, constant diameter from its distal end to the proximal end of the sheath hub 1002. The distal end of the sheath 1000 is situated within the aortic outflow tract, proximate the aortic root, with the sheath 1000 having fully traversed the aorta and aortic arch 108. In this and certain other embodiments, the distal region 1008 has been routed through the aortic arch and then expanded to remodel the walls of the expandable distal portion 1008 of the sheath

1000. In its remodeled configuration, the distal expandable region 1008 exhibits greater stiffness, reduced flexibility, greater diameter, and greater torqueability than the distal expandable region 1008 in its unexpanded configuration as illustrated in FIG. 10. The remodeling generally is preferable to elastic deformation that can cause the distal region 1008 of the sheath to spring or bias itself straight, since the remodeling can result in a sheath that generally takes on the curve to which it is pre-set prior to expansion and to which the distal region 1008 is exposed during the expansion procedure. The remodeling condition occurs because balloon dilatation forces cause the plastic walls of the distal end 1008 of the sheath 1000 to plastically flow to their new configuration prior to removal of the dilator. The reinforcement within the distal, expandable region 1008 preferably does not substantially contribute to bending forces on the expanded distal section 1008.

FIG. 12 illustrates the patient 100 wherein a prosthetic aortic heart valve replacement 620 is being placed through the sheath 1000 by means of a catheter valve introducer 622. The catheter valve introducer 622 is placed through a hemostasis valve 1002 affixed at or near the proximal end of the sheath 1000. The sheath 1000 facilitates introduction of the prosthetic valve 620 as well as its removal, should that become necessary. The guidewire 210 can remain in place as a safety wire or it can be removed during this part of the procedure. The distal expandable region 1008 of the sheath 1000 is fully expanded, is relatively rigid compared to its collapsed configuration as illustrated in FIG. 10, and is less capable of being advanced through tortuous vasculature than when it is in its un-dilated state.

Figure 13:
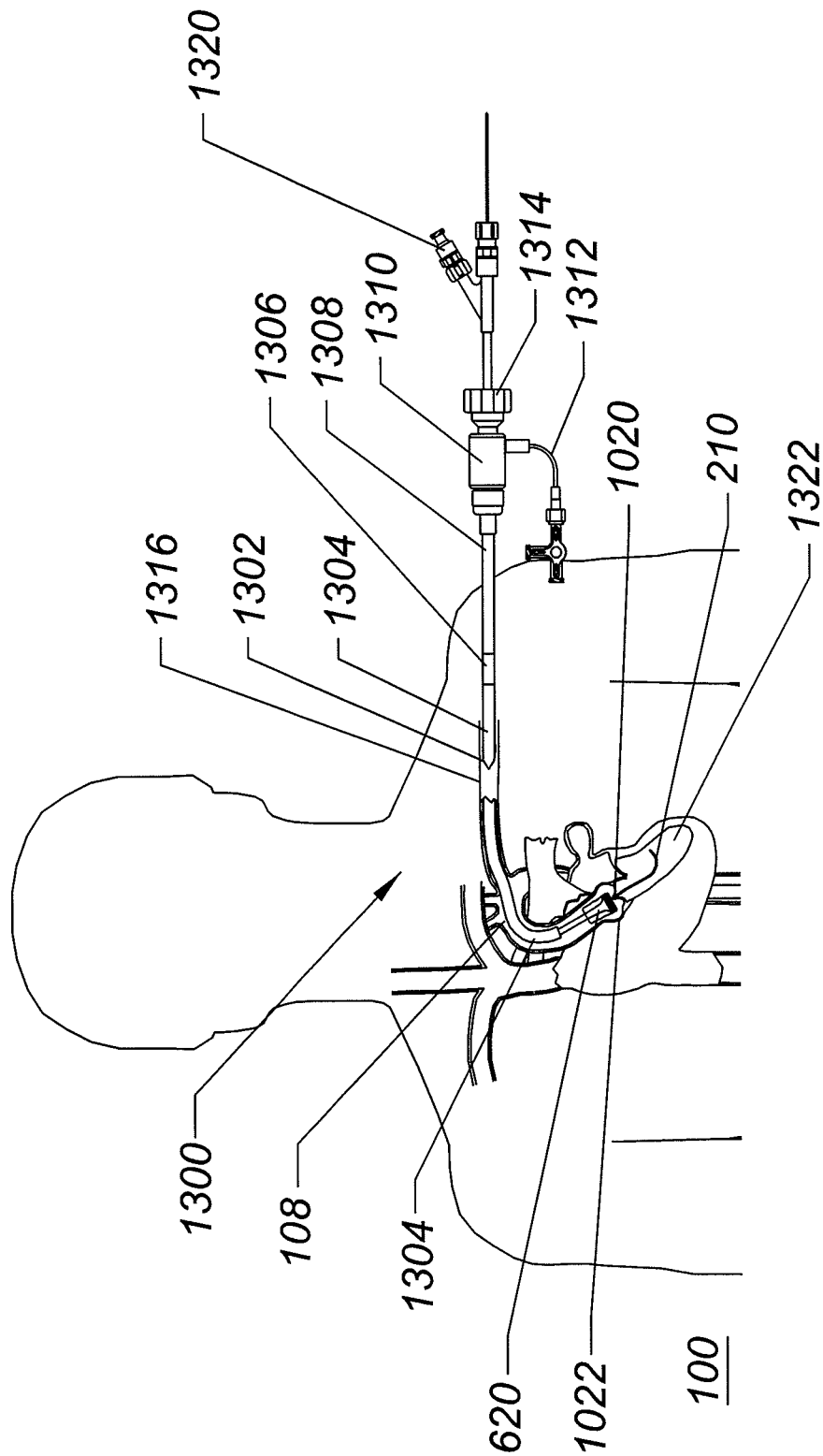
FIG. 13 illustrates a prosthetic aortic heart valve replacement being placed through a subclavian artery access sheath, according to an embodiment of the invention.

FIG. 13 illustrates an expandable arterial access sheath 1300 being used to access the arterial vasculature through the left subclavian artery 1316 of a human patient 100. The expandable arterial access sheath 1300 enters the subclavian artery 1316 at the arterial access site 1302. The sheath 1300 comprises the expandable distal region 1304, the transition zone 1306, the proximal, non-expandable region 1308, the sheath hub 1310, and the sheath hemostasis valve 1314. The sheath 1300 is being used to guide a valve delivery catheter 1320 to the aortic outflow tract 1022 through the aortic arch 108 and proximate the natural aortic valve 1020. A guidewire 210 is illustrated passing through the central lumen (not shown) of the valve delivery catheter 1320 with the distal end of the guidewire 210 extending through the natural aortic valve 1020 and into the left ventricle 1322. The valve delivery catheter 1320 is being used to deliver, in retrograde fashion, a prosthetic aortic valve 620, which is in its diametrically collapsed, first configuration.

Referring to FIG. 13, the subclavian access configuration of the expandable arterial access sheath 1300 is shorter than a trans-femoral device with a working length that can range between 25 and 50 cm. The same diameters and construction techniques used for other devices described herein are suitable for use in the expandable subclavian access sheath 1300. It is generally advantageous that the expandable distal region 1304 is inserted into the arterial access site 1302 and advanced to a region just downstream of, or through, the natural, diseased or damaged aortic valve 1020. The transition zone 1306 and the proximal, non-expandable region advantageously reside outside the body for the duration of the procedure such that no sheath axial translation occurs after the expandable distal region 1304 has been dilated or expanded.

Figure 14A:
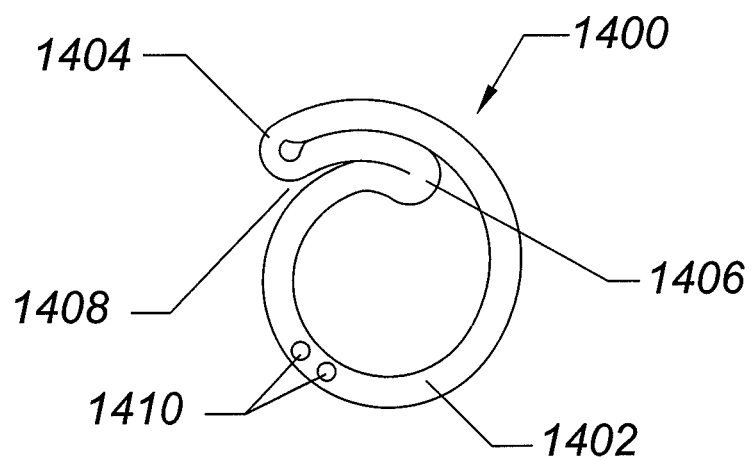
FIG. 14A illustrates a lateral cross-section of a distal region of an expandable arterial sheath comprising a single fold, according to an embodiment of the invention.

FIG. 14A illustrates a lateral cross-section view of a distal region 1400 of an expandable arterial sheath comprising a wall 1402, a single longitudinally extending fold 1408 further comprising an outside edge 1404 and an inside edge 1406, and a plurality of electrical conductors running axially through the wall 1402. With a small diameter distal section 1400 and a relatively thick wall 1402, a single fold 1408 is the one structure to create during manufacturing. The sheath wall 1402 further comprises an optional electrical bus 1412 fabricated from stainless steel, silver, copper, or other conductor metal for use in transmitting electrical energy from the sheath hub (not shown) to distal regions of the sheath for purposes such as resistive heating, steering, or the like.

Figure 14B:
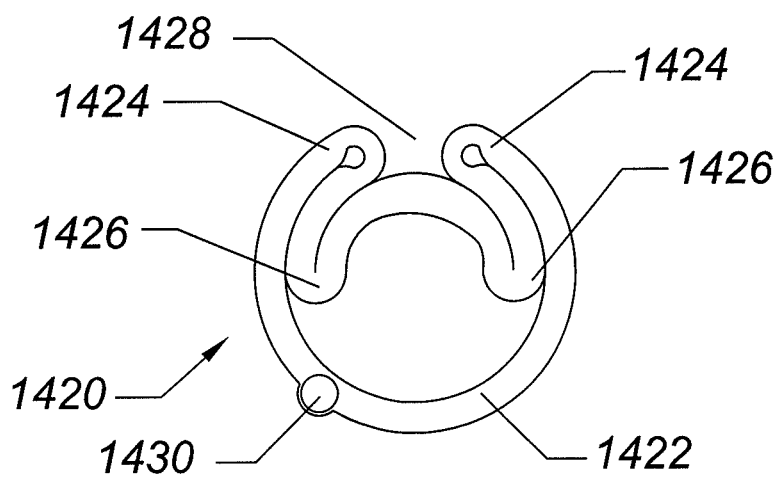
FIG. 14B illustrates a lateral cross-section of a distal region of an expandable arterial sheath comprising a double fold, according to an embodiment of the invention.

FIG. 14B illustrates another embodiment of a lateral cross-section of a distal region 1420 of an expandable arterial sheath comprising a wall 1422 further comprising a double longitudinally extending fold 1428. The double fold 1428 further comprises two outside edges 1424 and two inside edges 1426 which form longitudinal creases in the wall 1422. When the diameter of the sheath increases, it becomes advantageous to form a plurality of folds in the wall 1422. For a sheath having a fully expanded outside diameter ranging between 12 French and 30 French and with a wall thickness ranging between 1 and 2-French, a double fold, as illustrated in FIG. 14B is preferred. A double fold, for example can allow a 14 French outside diameter sheath to fold into a collapsed diameter of around 9 to 12 French. An 18-French outside diameter sheath having a 1 to 2-French wall thickness can be folded into a collapsed diameter of around 12 to 13 French using a double fold. The sheath wall 1422 further comprises an optional balloon inflation lumen 1430 for use in transmitting fluidic pressure or energy from the sheath hub to distal regions of the sheath wherein a balloon may be affixed. The diameter of the balloon inflation lumen 1430 can range between 0.005 to 0.025 inches. In other embodiments, the number of folds can range in number between 3 and 10.

It should be appreciated in the embodiments described above that the longitudinal folds of FIGS. 14A and 14B or modifications thereof can be used to provide an expandable region of the catheter (see embodiments of FIGS. 3A-13) with an initial small cross-sectional diameter. By unfolding the distal region 1400, the diameter of the distal region can be increased to a larger diameter. In the smaller folded configuration, the malleable structures described above can maintain the distal region in the smaller folded configuration. In other embodiments, an external structure can maintain the sheath in the folded configuration. In this smaller folder configuration it has been noted that the flexibility of the catheter (e.g., the ability of the catheter to navigate the aortic arch) is increased. When the catheter is unfolded and expanded, the malleable structure can reform to the larger unfolded diameter and to the shape of the anatomy (e.g., the aortic arch) in which the sheath his placed. In the unfolded configuration, the malleable structures provide hoop strength maintain the patency of the lumen.

It also should be noted that certain objects and advantages of the invention have been described above for the purpose of describing the invention and the advantages achieved over the prior art. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Moreover, although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. For example, it is contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow

We claim:

1. An endovascular intra-aortic catheter for providing access to a patient's heart through an aortic passageway leading away from an aortic valve in the patient's heart; the catheter comprising:
   a sheath having a distal portion, a proximal portion and a lumen extending therebetween, the sheath having a length between a distal end of the distal portion and a proximal end of the proximal portion, the length being sufficient such that the proximal end of the proximal portion extends out of the patient at a puncture site into an iliac artery and the distal end of the distal portion adapted to extend at least to the patient's aortic arch; the distal portion of the sheath comprising at least one diametrically expandable region that comprises a malleable reinforcement structure configured to maintain the at least one diametrically expandable region in a first cross-sectional configuration in which the at least one diametrically expandable region is longitudinally folded into a reduced cross-sectional profile and can be expanded to a second cross-sectional configuration in which the at least one diametrically expandable region is unfolded into a larger cross-sectional profile; and
   a hub coupled to the sheath at its proximal end.

2. The catheter of claim 1, wherein in the first cross-sectional configuration the at least one diametrically expandable region is longitudinally more flexible than in the second cross-sectional configuration.

3. The catheter of claim 1, further comprising a dilator pre-positioned within the sheath.

4. The catheter of claim 1, further comprising a braided reinforcement member on the distal end of the sheath that is configured such that a proximal directed tension on the distal end of the sheath causes axial compression of the braided reinforcement member in the sheath wall resulting in diametric expansion of the sheath.

5. The catheter of claim 1, further comprising a second expandable region located distally to the first expandable region, wherein the second expandable region is configured to have reduced capability of maintaining its cross-sectional shape relative to the first expandable region.

6. The catheter of claim 5, further comprising a third expandable region located distally to the second expandable region, further wherein the third expandable region is shorter than the second expandable region and has increased capability of maintaining its cross-sectional shape relative to the second expandable region but less capability of maintaining its cross-sectional shape than the first expandable region.

7. The catheter of claim 1, wherein the expandable region comprises an elastic or semi-elastic wall.

8. The catheter of claim 7, wherein the expandable region comprises an elastic or semi-elastic wall further reinforced with an internal braid.

9. The catheter of claim 1, further comprising hemostasis valves at the proximal end of the sheath to prevent excessive loss of blood from the patient.

10. The catheter of claim 1, further comprising a pre-inserted dilator.

11. The catheter of claim 1, further comprising a pre-inserted balloon dilator, wherein the balloon dilator comprises a non-distensible high-pressure balloon disposed along at least the entire length of the expandable region.

12. The catheter of claim 1, wherein the expandable introduction sheath length is sufficient to span the distance from an insertion point in the iliac artery to a region anatomically proximal to the aortic bifurcation.

13. The catheter of claim 1, wherein the expandable region expands from a first, smaller outside diameter of approximately 16 French or less to a second, larger outside diameter of approximately 32 French.

14. The catheter of claim 1, further comprising nitinol reinforcing elements within the expandable region.

15. The catheter of claim 14, wherein the nitinol reinforcing elements are biased to diametrically expand the expandable region.

16. The catheter of claim 14, wherein the nitinol reinforcing elements are biased to diametrically collapse the expandable region.

17. The catheter of claim 14, wherein the nitinol elements comprise shape-memory properties that are fully activated at about body temperature.

18. The catheter of claim 14, wherein the nitinol elements comprise shape-memory elements that are fully activated at temperatures above body temperature.

19. The catheter of claim 1, wherein the malleable reinforcement structure comprises a flat wire wound into a coil.

20. An endovascular introducer catheter system for providing access to a patient's vascular system; the catheter comprising:
   a sheath having a distal portion, a proximal portion and a lumen extending therebetween, the sheath comprising at least one diametrically expandable region that comprises a malleable reinforcement structure configured to maintain the at least one diametrically expandable region in a first cross-sectional configuration in which the at least one diametrically expandable region is longitudinally folded into a reduced cross-sectional profile and can be expanded to a second cross-sectional configuration in which the at least one diametrically expandable region is unfolded into a larger cross-sectional profile;
   a hub coupled to the sheath at its proximal end; and
   an implantable device delivery catheter comprising an implantable device advanced through the lumen of the sheath.

21. The catheter system of claim 20, wherein the sheath comprises a braided reinforcing structure on both the proximal portion and the distal portion of the sheath.

22. The catheter system of claim 20, wherein the proximal portion comprises a coil reinforcement fabricated from spring metal.

23. The catheter system of claim 20, wherein the proximal portion comprises a coil reinforcement fabricated from spring hardness stainless steel.

24. The catheter system of claim 20, wherein the proximal portion comprises both a coil and a braid reinforcement embedded within a polymeric surround.

25. The catheter system of claim 20, further comprising a hemostasis valve affixed to the proximal end of the sheath.

26. The catheter system of claim 20, wherein the diametrically expandable region comprises the malleable reinforcement structure embedded between two layers of polymer, further wherein the malleable reinforcement structure does not substantially move relative to the two layers of polymer when the sheath is expanded from its first cross-sectional configuration to its second cross-sectional configuration.

27. The catheter system of claim 20, wherein the implantable device is a heart valve.

* * * * *